(12) United States Patent
Akagane

(10) Patent No.: US 9,180,315 B2
(45) Date of Patent: Nov. 10, 2015

(54) ULTRASONIC TREATMENT DEVICE AND PROBE UNIT

(71) Applicant: OLYMPUS CORPORATION, Tokyo (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/773,023

(22) Filed: Feb. 21, 2013

(65) Prior Publication Data
US 2013/0226041 A1    Aug. 29, 2013

Related U.S. Application Data

(63) Continuation of application No. PCT/JP2012/065510, filed on Jun. 18, 2012.

(60) Provisional application No. 61/498,779, filed on Jun. 20, 2011.

(51) Int. Cl.
| | |
|---|---|
| *A61N 7/00* | (2006.01) |
| *A61B 17/32* | (2006.01) |
| *A61B 17/00* | (2006.01) |
| *A61B 17/22* | (2006.01) |

(52) U.S. Cl.
CPC .......... *A61N 7/00* (2013.01); *A61B 17/320068* (2013.01); *A61B 17/320092* (2013.01); *A61B 2017/00473* (2013.01); *A61B 2017/22015* (2013.01); *A61B 2017/320084* (2013.01); *A61B 2217/005* (2013.01)

(58) Field of Classification Search
USPC ....................... 600/439, 459; 601/2
See application file for complete search history.

(56) References Cited

U.S. PATENT DOCUMENTS

| | | | | |
|---|---|---|---|---|
| 4,804,364 | A | * | 2/1989 | Dieras et al. ............. 604/22 |
| 4,838,853 | A | * | 6/1989 | Parisi ...................... 604/22 |
| 4,922,902 | A | | 5/1990 | Wuchinich et al. |

(Continued)

FOREIGN PATENT DOCUMENTS

| | | |
|---|---|---|
| CN | 101018510 A | 8/2007 |
| JP | A-63-500572 | 3/1988 |

(Continued)

OTHER PUBLICATIONS

Engineering fit, Published by Wikipedia, the free encyclopedia Dated Oct. 9, 2008.*

(Continued)

*Primary Examiner* — Katherine Fernandez
*Assistant Examiner* — Michael Kellogg
(74) *Attorney, Agent, or Firm* — Oliff PLC

(57) ABSTRACT

An ultrasonic treatment device includes a vibration transmitting section transmitting an ultrasonic vibration to a distal end of an ultrasonic probe, and a hole defining portion extended toward a proximal direction along the longitudinal axis from a distal end portion of the vibration transmitting section and defining a hole-shaped portion inside the vibration transmitting section. The ultrasonic treatment device includes a tube member extended inside the vibration transmitting section and including a tube distal end which is connected to the hole defining portion of the vibration transmitting section at a first node position of the ultrasonic vibration to a distal direction side of a piezoelectric element.

5 Claims, 18 Drawing Sheets

(56) References Cited

U.S. PATENT DOCUMENTS

| | | | |
|---|---|---|---|
| 5,464,389 A | 11/1995 | Stahl | |
| 5,484,398 A * | 1/1996 | Stoddard | 604/22 |
| 5,527,273 A | 6/1996 | Manna et al. | |
| 5,582,588 A | 12/1996 | Sakurai et al. | |
| 5,807,307 A * | 9/1998 | Parisi et al. | 604/22 |
| 6,214,017 B1 | 4/2001 | Stoddard et al. | |
| 7,018,389 B2 * | 3/2006 | Camerlengo | 606/166 |
| 7,220,233 B2 * | 5/2007 | Nita et al. | 601/2 |
| 7,645,245 B2 * | 1/2010 | Sekino et al. | 601/4 |
| 8,574,175 B2 * | 11/2013 | Yamada | 601/3 |
| 2003/0036705 A1 * | 2/2003 | Hare et al. | 600/437 |
| 2004/0158151 A1 * | 8/2004 | Ranucci et al. | 600/439 |
| 2006/0253050 A1 * | 11/2006 | Yoshimine et al. | 601/2 |
| 2008/0103430 A1 * | 5/2008 | Gomez | 604/20 |
| 2008/0194999 A1 | 8/2008 | Yamaha et al. | |
| 2009/0216246 A1 * | 8/2009 | Nita et al. | 606/128 |
| 2010/0036388 A1 * | 2/2010 | Gomez | 606/107 |
| 2010/0137751 A1 * | 6/2010 | Tadami | 601/2 |
| 2010/0274269 A1 * | 10/2010 | Song et al. | 606/159 |
| 2010/0312111 A1 * | 12/2010 | Tanaka et al. | 600/443 |
| 2013/0345734 A1 * | 12/2013 | Cotter et al. | 606/169 |

FOREIGN PATENT DOCUMENTS

| | | |
|---|---|---|
| JP | A-04-152942 | 5/1992 |
| JP | A-11-332873 | 12/1999 |
| JP | A-2001-161705 | 6/2001 |
| JP | A-2003-525063 | 8/2003 |
| JP | A-2005-137481 | 6/2005 |
| JP | A-2008-194457 | 8/2008 |
| WO | 9933665 A1 | 7/1999 |

OTHER PUBLICATIONS

Office Action issued in Japanese Application No. 2013-508704 dated Apr. 23, 2013 (with translation).

International Search Report issued in International Application No. PCT/JP2012/065510 dated Sep. 11, 2012 (with translation).

Translation of Sep. 11, 2012 Written Opinion of the International Searching Authority issued in International Patent Application No. PCT/JP2012/065510.

Translation of Jan. 9, 2014 International Preliminary Report on Patentability issued in International Patent Application No. PCT/JP2012/065510.

Nov. 10, 2014 Search Report issued in European Application No. 12803387.5.

Jun. 11, 2015 Office Action issued in Chinese Patent Application No. 201280026495.4.

\* cited by examiner

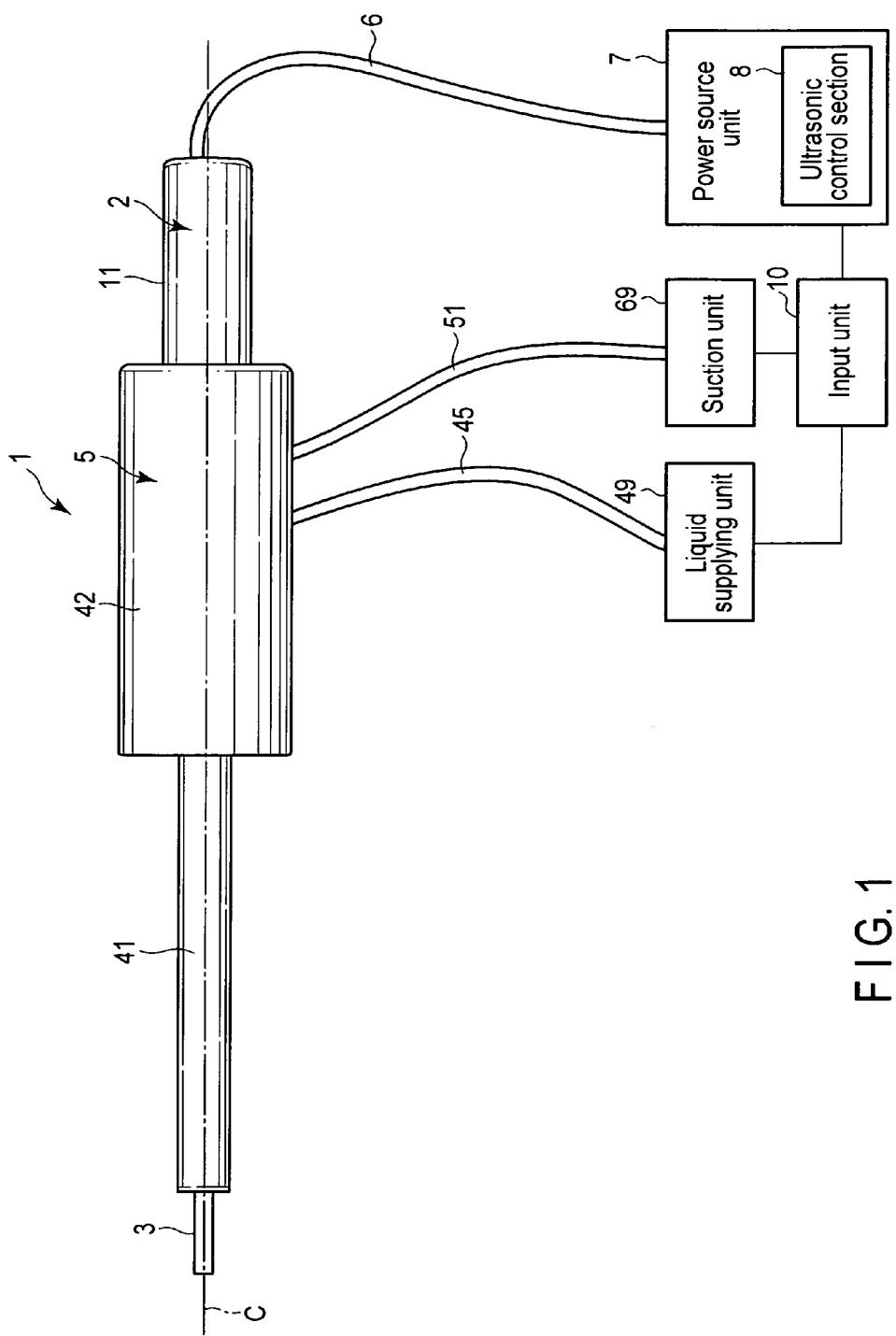
F I G. 1

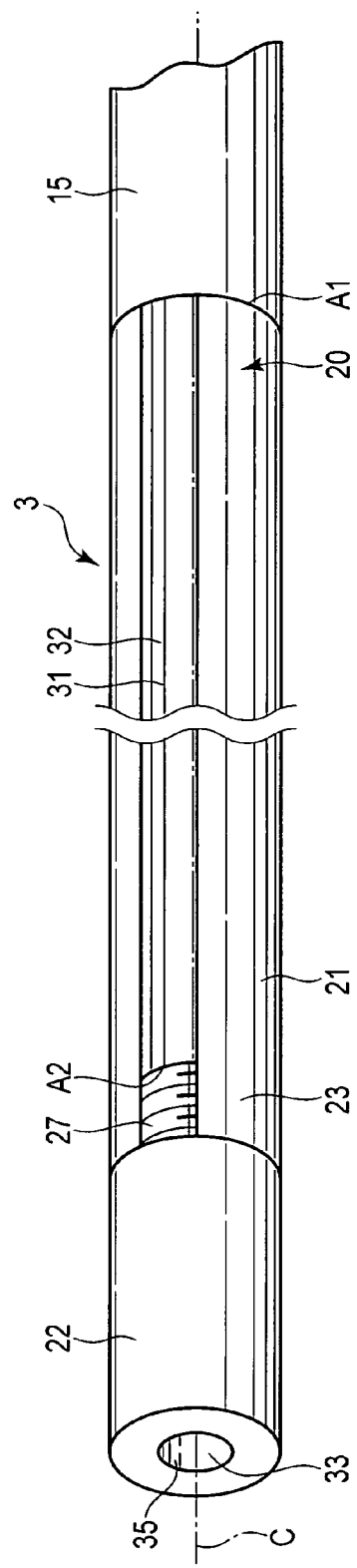
F I G. 3

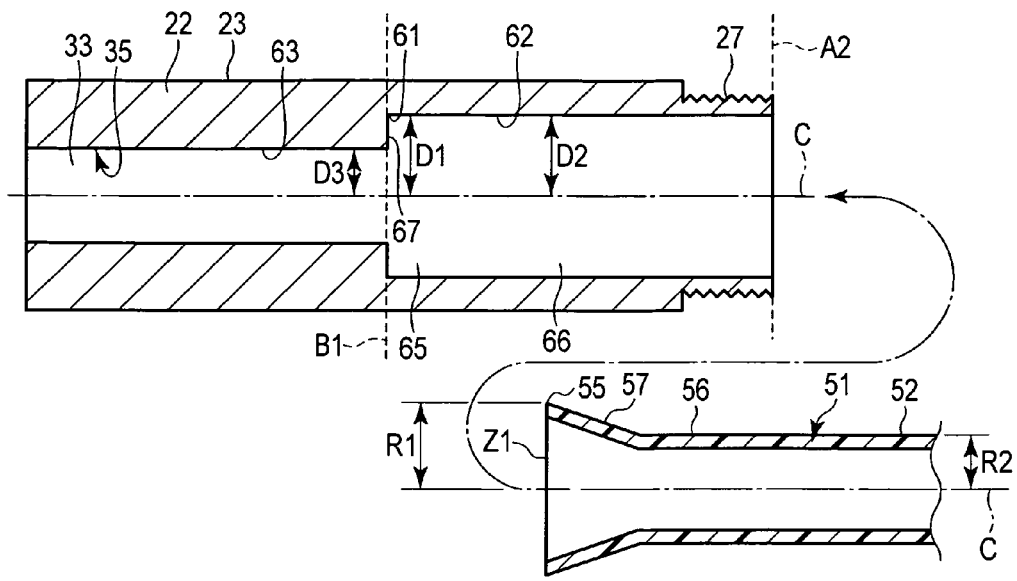
F I G. 9
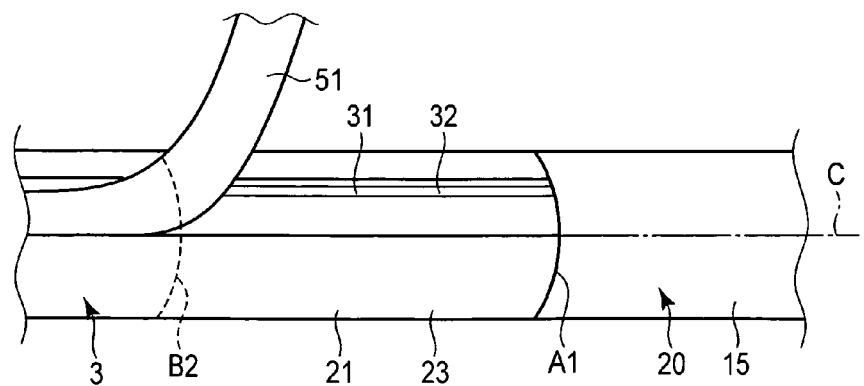
F I G. 10

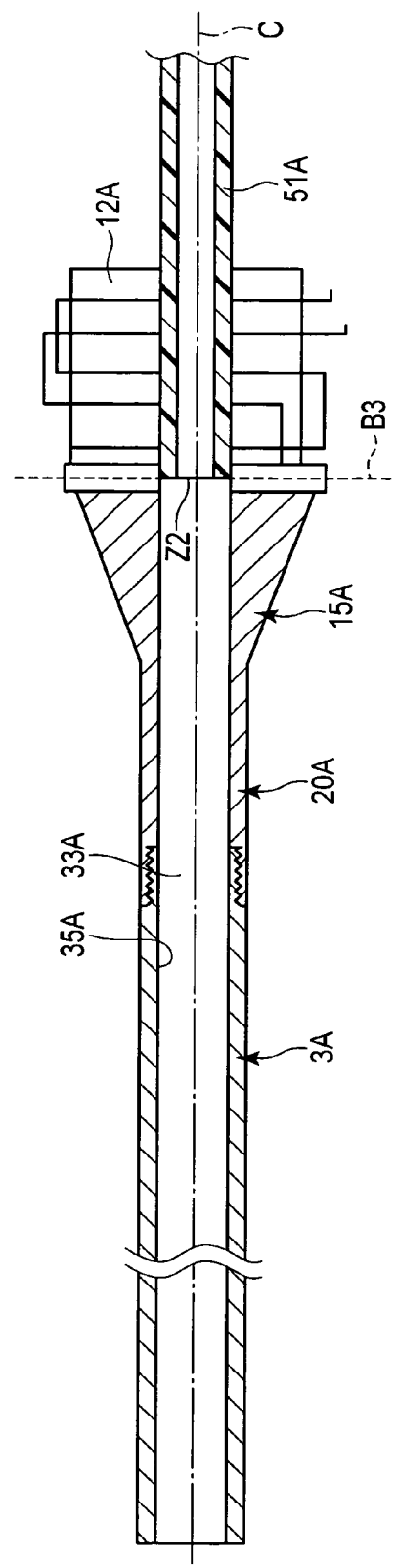
F I G. 11

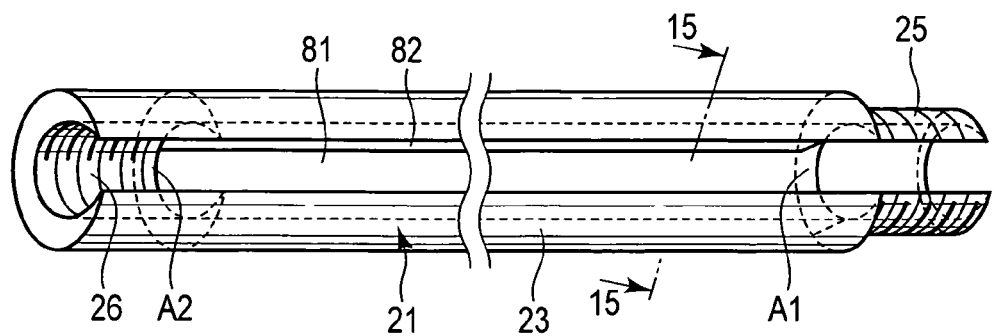
F I G. 14
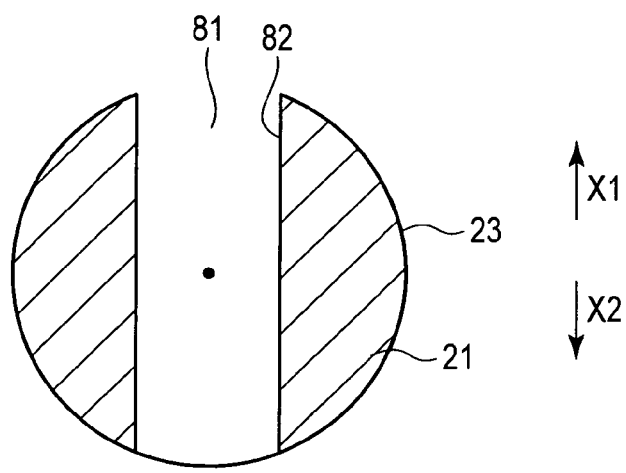
F I G. 15

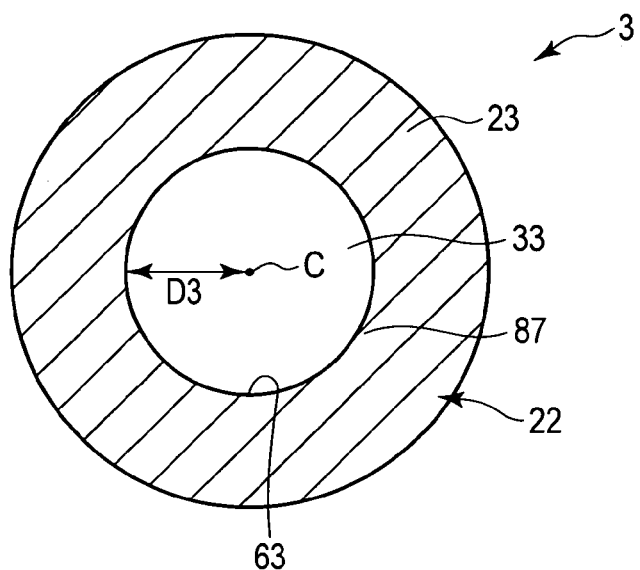
F I G. 19
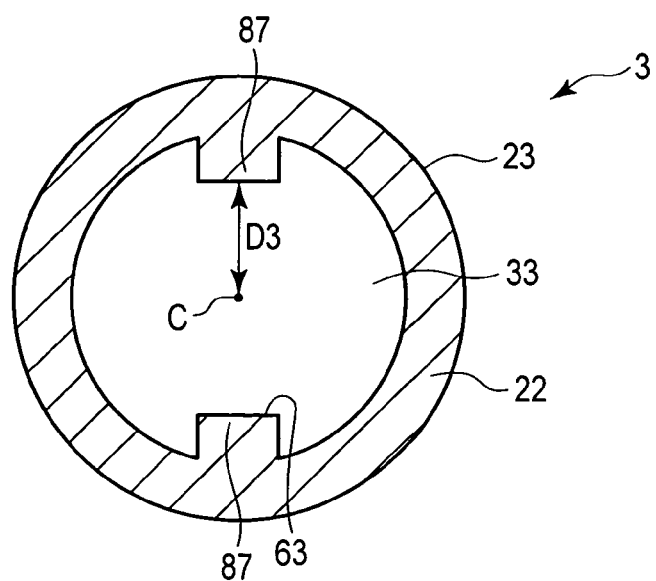
F I G. 20

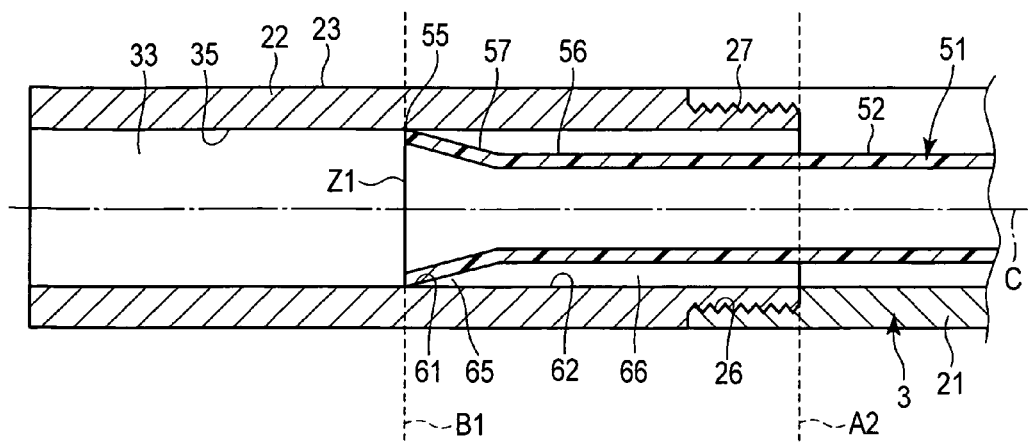
F I G. 21
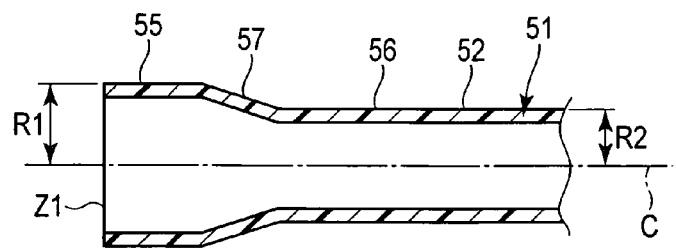
F I G. 22
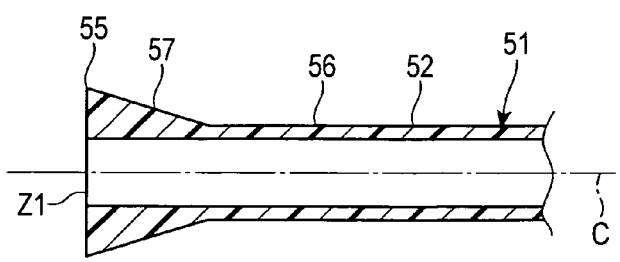
F I G. 23

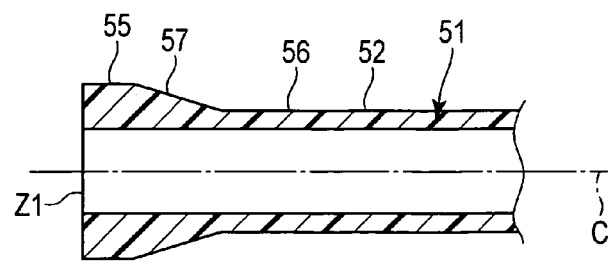
F I G. 24
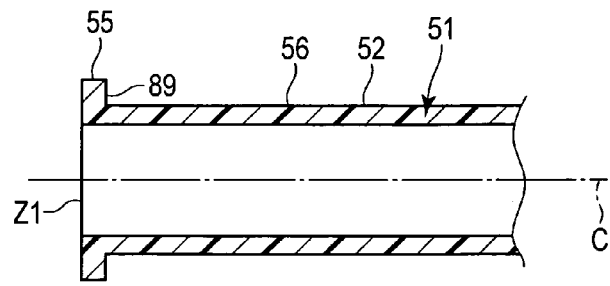
F I G. 25
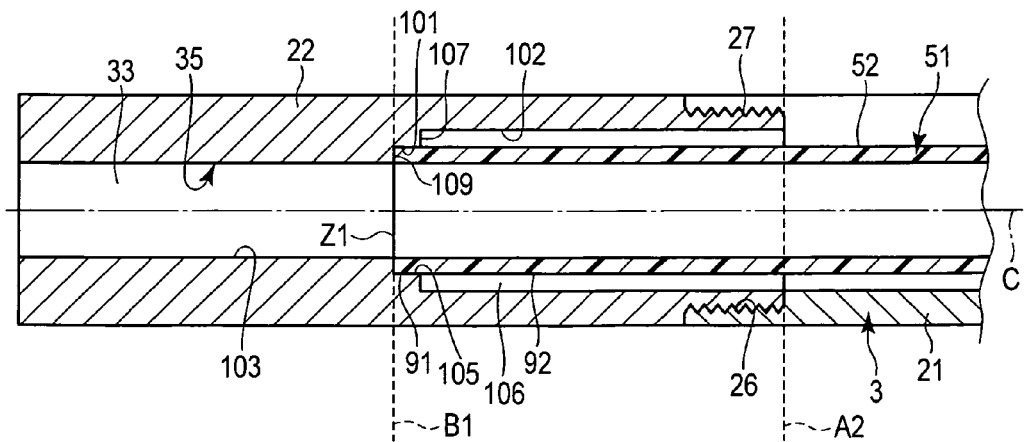
F I G. 26

ULTRASONIC TREATMENT DEVICE AND PROBE UNIT

CROSS-REFERENCE TO RELATED APPLICATIONS

This is a Continuation Application of PCT Application No. PCT/JP2012/065510, filed Jun. 18, 2012 and based upon and claiming the benefit of priority from prior U.S. Provisional Application No. 61/498,779, filed Jun. 20, 2011, the entire contents of which are incorporated herein by reference.

BACKGROUND OF THE INVENTION

1. Field of the Invention

The present invention relates to an ultrasonic treatment device configured to perform an ultrasonic treatment including ultrasonic suction, and a probe unit provided in the ultrasonic treatment device.

2. Description of the Related Art

In Jpn. Pat. Appln. KOKAI Publication No. 2005-137481, there is disclosed an ultrasonic treatment device (ultrasonic surgical device) configured to perform a treatment called ultrasonic suction. This ultrasonic treatment device includes an ultrasonic vibrator (ultrasonic oscillator) configured to generate ultrasonic vibration. A horn, which is an amplitude enlarging section configure to enlarge an amplitude of the ultrasonic vibration, is provide to a distal direction side of the ultrasonic vibrator. An ultrasonic probe extended along a longitudinal axis is provided to the distal direction side of the horn. The ultrasonic vibration generated by the ultrasonic vibrator is transmitted to a distal end of the ultrasonic probe. That is, the ultrasonic vibrator, the horn and the ultrasonic probe constitute a vibration transmitting section configured to transmit the ultrasonic vibration.

The ultrasonic suction is performed by using a distal surface of the ultrasonic probe which ultrasonically vibrates, and is performed by using a physical phenomenon called cavitation. Specifically, the ultrasonic probe repeats high speed vibration several ten thousand times per second by the ultrasonic vibration, and hence a pressure periodically fluctuates in a vicinity of the distal surface of the ultrasonic probe. When the pressure in the vicinity of the distal surface becomes lower than a saturated vapor pressure only for a very short time by the pressure fluctuation, micro bubbles (cavities) are generated in a liquid of a body cavity or a liquid supplied (forwarded) from the ultrasonic treatment device to a vicinity of a position of a living tissue which is to be treated. Moreover, the generated bubbles disappear owing to a force which acts when the pressure in the vicinity of the distal surface increases (compresses). The above-mentioned physical phenomenon is called a cavitation phenomenon. By impact energy at the disappearance of the bubbles, a living tissue of, e.g. hepatic cells which do not have elasticity is shattered (crushed) and emulsified. In this case, a living tissue such as a blood vessel having a high elasticity is not easily shattered because the impact is absorbed, and the living tissue is selectively shattered.

Moreover, in the ultrasonic treatment device (ultrasonic surgical device) of Jpn. Pat. Appln. KOKAI Publication No. 2005-137481, a hole-shaped portion is extended from a distal end to a proximal end inside the vibration transmitting section. A tube member is inserted from a proximal direction side into the hole-shaped portion. The tube member inserted from an outside of the vibration transmitting section into the hole-shaped portion is a non-vibrating member which does not vibrate by the ultrasonic vibration. A distal end of the tube member is connected to the vibration transmitting section at a connection node position which is a node position of the ultrasonic vibration provided to the proximal direction side of the horn, the horn being the amplitude enlarging section. A region (part) of the hole-shaped portion disposed to the distal direction side of the connection node position communicates with an inside of the tube member. The living tissue shattered and emulsified by the cavitation passes through the region (part) of the hole-shaped portion to the distal direction side of the connection node position, and the inside of the tube member, from an opening of the hole-liked portion at the distal end of the ultrasonic probe, and the living tissue is suctioned (sucked). When the above action is continued, the living tissue is resected.

BRIEF SUMMARY OF THE INVENTION

According to one aspect of the invention, an ultrasonic treatment device includes that a vibration transmitting section which includes a piezoelectric element configured to generate ultrasonic vibration, and an ultrasonic probe extended to a distal direction side of the piezoelectric element along a longitudinal axis, and which is configured to transmit the ultrasonic vibration to a distal end of the ultrasonic probe; a hole defining portion which is extended toward a proximal direction along the longitudinal axis from a distal end portion of the vibration transmitting section, and which defines a hole-shaped portion inside the vibration transmitting section; and a tube member which is extended inside the vibration transmitting section, and which includes a tube distal end, the tube distal end being connected to the hole defining portion of the vibration transmitting section at a first node position of the ultrasonic vibration to the distal direction side of the piezoelectric element.

According to one another aspect of the invention, a probe unit includes that an ultrasonic probe which is extended along a longitudinal axis, and which is attachable to a distal direction side part of a piezoelectric element configured to generate ultrasonic vibration, the ultrasonic probe being configured to transmit the ultrasonic vibration from a proximal end to a distal end along the longitudinal axis; a hole defining portion which is extended toward a proximal direction along the longitudinal axis from a distal end portion of the ultrasonic probe, and which defines a hole-shaped portion inside the ultrasonic probe; and a tube member which is extended inside the ultrasonic probe, and which includes a tube distal end, the tube distal end being connected to the hole defining portion of the ultrasonic probe at a first node position of the ultrasonic vibration.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic view showing an ultrasonic treatment device according to a first embodiment of the present invention;

FIG. 3 is a perspective view schematically showing an ultrasonic probe according to the first embodiment;

FIG. 9 is a cross-sectional view schematically showing the cylindrical member of the ultrasonic probe and a tube member according to the first embodiment in a disassembled state;

FIG. 10 is a perspective view schematically showing an assembled state of the tube member and a probe main body of the ultrasonic probe according to the first embodiment;

FIG. 11 is a cross-sectional view schematically showing a vibration transmitting section according to a first comparative example;

FIG. 14 is a perspective view schematically showing a probe main body of an ultrasonic probe according to a second modification of the first embodiment;

FIG. 15 is a cross-sectional view taken along the line 15-15 of FIG. 14;

FIG. 19 is a cross-sectional view taken along the 19-19 line of FIG. 18;

FIG. 20 is cross-sectional view schematically showing a constitution of projecting portions of a cylindrical member of an ultrasonic probe according to a sixth modification of the first embodiment;

FIG. 21 is a cross-sectional view schematically showing an inner constitution of a cylindrical member of an ultrasonic probe according to a seventh modification of the first embodiment;

FIG. 22 is a cross-sectional view schematically showing a tube member according to an eighth modification of the first embodiment;

FIG. 23 is a cross-sectional view schematically showing a tube member according to a ninth modification of the first embodiment;

FIG. 24 is a cross-sectional view schematically showing a tube member according to a tenth modification of the first embodiment;

FIG. 25 is a cross-sectional view schematically showing a tube member according to an eleventh modification of the first embodiment;

FIG. 26 is a cross-sectional view schematically showing an inner constitution of a cylindrical member of an ultrasonic probe according to a second embodiment of the present invention;

Figure 2:
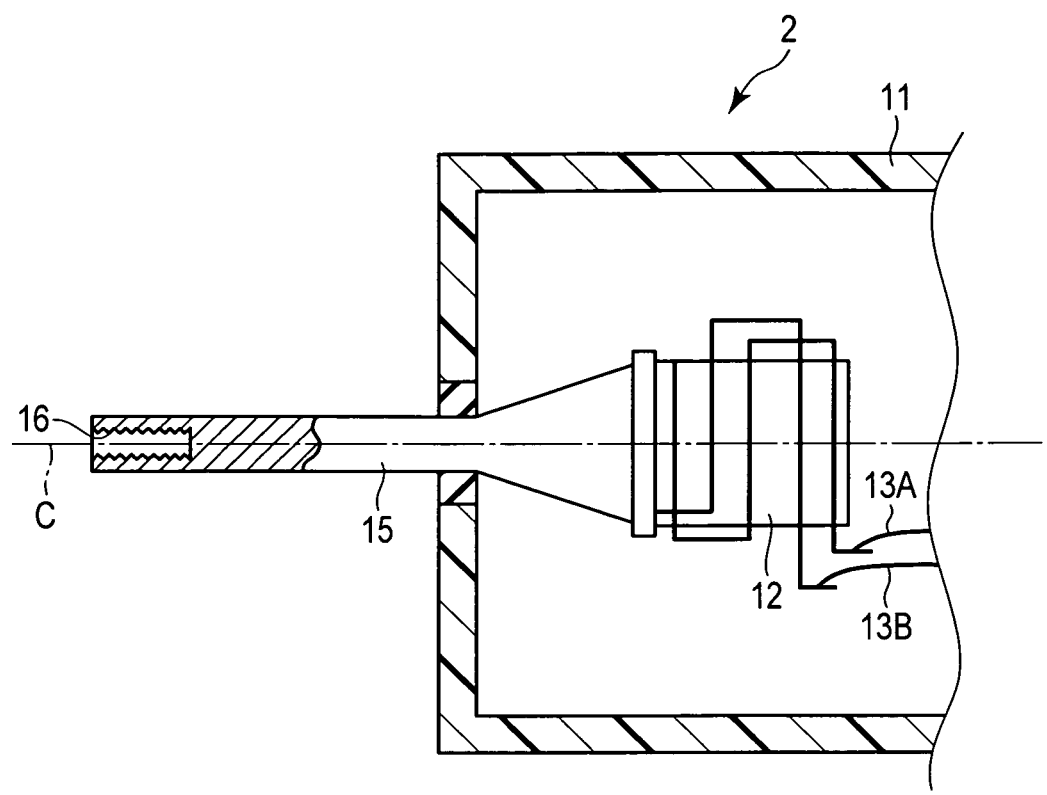
FIG. 2 is a cross-sectional view schematically showing a constitution of a vibrator unit according to the first embodiment.

DETAILED DESCRIPTION OF THE INVENTION (First Embodiment)

A first embodiment of the present invention will be described with reference to FIG. 1 to FIG. 12. FIG. 1 is a view showing an ultrasonic treatment device (ultrasonic surgical device) 1 of the present embodiment. It is to be noted that the ultrasonic treatment device 1 of the present embodiment is an ultrasonic suction device which selectively shatters (crushes) and resects a living tissue by cavitation caused by ultrasonic vibration, and suctions (sucks) the resected living tissue.

As shown in FIG. 1, the ultrasonic treatment device 1 includes a vibrator unit (oscillator unit) 2, an ultrasonic probe (a probe unit) 3, and a sheath unit 5.

The vibrator unit 2 includes a vibrator case (oscillator case) 11. To a proximal end of the vibrator case 11, one end of a cable 6 is connected. The other end of the cable 6 is connected to a power source unit 7. The power source unit 7 includes an ultrasonic control section 8. The power source unit 7 is connected to an input unit 10 such as a foot switch.

FIG. 2 is a view showing a constitution of the vibrator unit 2. As shown in FIG. 2, in the vibrator case 11, an ultrasonic vibrator (ultrasonic oscillator) 12 including a piezoelectric element configured to convert a current into the ultrasonic vibration is provided. To the ultrasonic vibrator 12, one end of each of electric signal lines 13A and 13B is connected. The electric signal lines 13A and 13B pass through an inside of the cable 6, and the other ends of the electric signal lines are connected to the ultrasonic control section 8 of the power source unit 7. When the current is supplied from the ultrasonic control section 8 to the ultrasonic vibrator 12 through the electric signal lines 13A and 13B, the ultrasonic vibration takes place in the ultrasonic vibrator 12. A horn 15, which is an amplitude enlarging section configured to enlarge an amplitude of the ultrasonic vibration, is coupled to a distal direction side of the ultrasonic vibrator 12. The horn 15 is attached to the vibrator case 11. The ultrasonic vibrator 12 and the horn 15 are formed into a columnar shape (non-hollow). Moreover, in a distal end portion of an inner peripheral surface of the horn 15, an internal thread portion 16 is formed.

Figure 4:
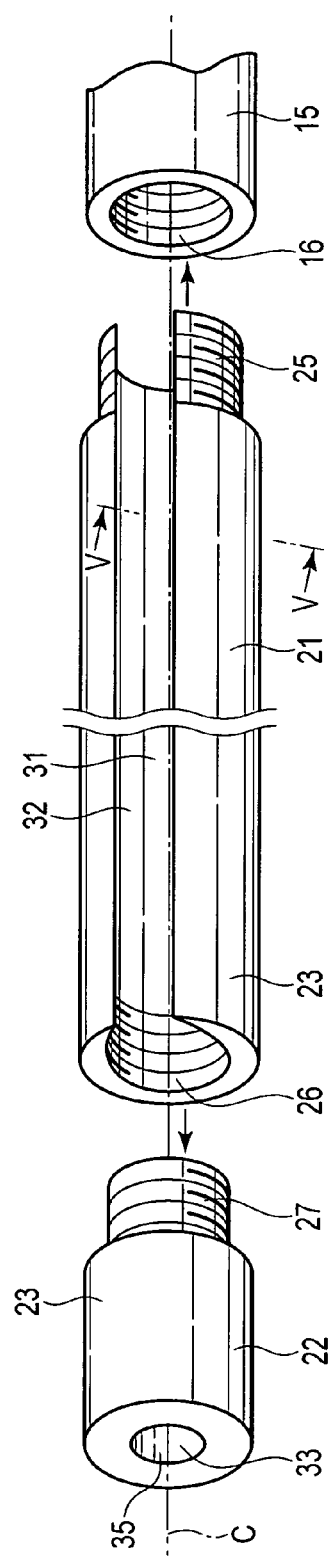
FIG. 4 is a perspective view schematically showing respective members of the ultrasonic probe according to the first embodiment in a disassembled state.

FIG. 3 and FIG. 4 are views showing a constitution of the ultrasonic probe 3. As shown in FIG. 3 and FIG. 4, the ultrasonic probe 3 is extended along a longitudinal axis C to a distal direction side of the horn 15. The ultrasonic probe 3 is formed by cutting in which a drill or the like is used, electric discharge machining, metal injection molding (MIM), or the like. The ultrasonic probe 3 includes a probe main body 21 and a cylindrical member 22. Moreover, the ultrasonic probe 3 includes an outer peripheral portion 23 extended along the longitudinal axis C.

In a proximal direction side region (part) of the probe main body 21, an external thread portion 25 is provided. When the external thread portion 25 is screwed into the internal thread portion 16 of the horn 15, the probe main body 21 of the ultrasonic probe 3 is attached to the distal direction side of the horn 15. Moreover, in a distal direction side region (part) of the probe main body 21, an internal thread portion 26 is provided. The cylindrical member 22 is connected to the distal direction side of the probe main body 21. In a proximal end portion of the cylindrical member 22, an external thread portion 27 is provided. When the external thread portion 27 is screwed into the internal thread portion 26 of the probe main body 21, the cylindrical member 22 is connected to the probe main body 21.

When the probe main body 21 is attached to the horn 15 and the cylindrical member 22 is connected to the probe main body 21, the ultrasonic vibration generated by the ultrasonic vibrator 12 is transmitted to a distal end of the cylindrical member 22 (a distal end of the ultrasonic probe 3) through the horn 15 and the probe main body 21. In this case, the ultrasonic vibrator 12, the horn 15 and the ultrasonic probe 3 form a vibration transmitting section 20 configured to transmit the ultrasonic vibration. The vibration transmitting section 20 vibrates by the ultrasonic vibration. The ultrasonic vibration is longitudinal vibration in which a vibration transmitting direction matches a vibrating direction. Moreover, a proximal end and a distal end of the vibration transmitting section 20 are anti-node positions of the ultrasonic vibration. It is to be noted that the outer peripheral portion 23 of the ultrasonic probe 3 is preferably provided with a stepped portion. In consequence, the amplitude of the ultrasonic vibration, which has been enlarged by the horn 15, is further enlarged.

Figure 5:
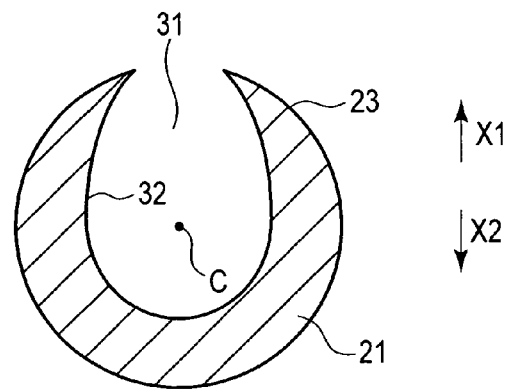
FIG. 5 is a cross-sectional view taken along the V-V line of FIG. 4.

FIG. 5 is a cross-sectional view taken along the V-V line of FIG. 4. As shown in FIG. 3 to FIG. 5, the probe main body 21 includes a groove defining portion 32 which defines a groove-shaped portion 31 along the longitudinal axis C. The groove-shaped portion 31 is recessed from a first perpendicular direction (a direction of an arrow X1 of FIG. 5), which is perpendicular to the longitudinal axis C, to a second perpendicular direction (a direction of an arrow X2 of FIG. 5), which is opposite to the first perpendicular direction. That is, the groove-shaped portion 31 which is a void portion is extended from the first perpendicular direction perpendicular to the longitudinal axis C to the second perpendicular direction. Moreover, a first perpendicular direction side end of the groove defining portion 32 which is a void regulating portion is continuous with the outer peripheral portion 23 of the ultrasonic probe 3.

As shown in FIG. 3, while the probe main body 21 is attached to the horn 15, a position of a distal end of the horn 15 substantially coincides with (matches) a position of a proximal end of the groove defining portion 32 in directions parallel to the longitudinal axis C. Therefore, while the probe main body 21 is attached to the horn 15, the groove-shaped portion 31 is extended along the longitudinal axis C from the distal end of the horn 15 (the proximal end of the groove defining portion 32). Moreover, while the cylindrical member 22 is connected to the probe main body 21, a position of a proximal end of the cylindrical member 22 substantially coincides with (matches) a position of a distal end of the groove defining portion 32 in the directions parallel to the longitudinal axis C. Therefore, while the cylindrical member 22 is connected to the probe main body 21, the groove-shaped portion 31 is extended along the longitudinal axis C to the proximal end of the cylindrical member 22 (the distal end of the groove defining portion 32).

Moreover, in the cylindrical member 22 (in the vibration transmitting section 20), a hole-shaped portion 33 is defined along the longitudinal axis C by a hole defining portion 35. The hole defining portion 35 is extended along the longitudinal axis C from the distal end of the cylindrical member 22 (a distal end portion of the vibration transmitting section 20). While the cylindrical member 22 is connected to the probe main body 21, a distal end of the groove-shaped portion 31 communicates with the hole-shaped 33.

While the probe main body 21 is attached to the horn 15 and the cylindrical member 22 is connected to the probe main body 21, the distal end of the horn 15 (the proximal end of the groove defining portion 32) is a first anti-node position A1 of the ultrasonic vibration. Moreover, the proximal end of the cylindrical member 22 (the distal end of the groove defining portion 32) is a second anti-node position A2 of the ultrasonic vibration which is different from the first anti-node position A1. Therefore, while the probe main body 21 is attached to the horn 15 and the cylindrical member 22 is connected to the probe main body 21, the groove-shaped portion 31 is defined along the longitudinal axis C from the first anti-node position A1 to the second anti-node position A2 by the groove defining portion 32.

Here, at the first anti-node position A1, a cross-sectional shape of the vibration transmitting section 20 which is perpendicular to the ultrasonic vibration transmitting direction and vibrating direction (the longitudinal axis C) changes. That is, the cross-sectional shape of the vibration transmitting section 20 which is perpendicular to the longitudinal axis C changes from a columnar shape which is point symmetrical about (around) the longitudinal axis C to a concaved shape which is not point symmetrical about the longitudinal axis C, at the first anti-node position A1. Similarly, at the second anti-node position A2, the cross-sectional shape of the vibration transmitting section 20 which is perpendicular to the ultrasonic vibration transmitting direction and vibrating direction (the longitudinal axis C) changes. That is, the cross-sectional shape of the vibration transmitting section 20 which is perpendicular to the longitudinal axis C changes from the concaved shape which is not point symmetrical about the longitudinal axis C to a cylindrical shape which is point symmetrical about the longitudinal axis C to, at the second anti-node position A2.

As shown in FIG. 1, the sheath unit 5 includes a sheath 41, and a holding case 42 coupled to a proximal direction side of the sheath 41. The ultrasonic probe 3 is inserted through the sheath 41. The sheath 41 is inserted from the distal direction side into the holding case 42, and the vibrator unit 2 is inserted from the proximal direction side into the holding case. In the holding case 42, the sheath 41 is connected to the vibrator case 11.

Figure 6:
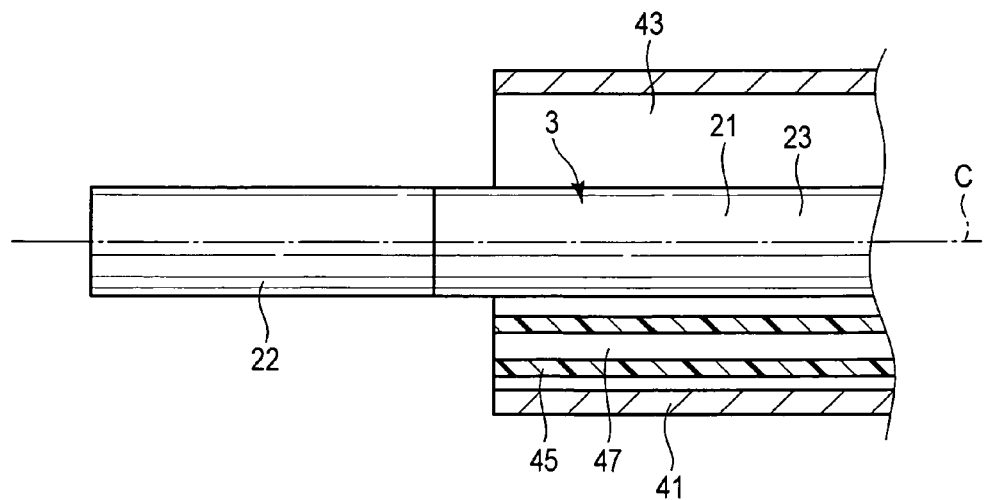
FIG. 6 is a cross-sectional view schematically showing a distal end portion of the ultrasonic probe and a distal end portion of a sheath according to the first embodiment.

FIG. 6 is a view showing a distal end portion of the sheath 41 and a distal end portion of the ultrasonic probe 3. As shown in FIG. 6, a space portion 43 is formed between the outer peripheral portion 23 of the ultrasonic probe 3 and the sheath 41. In the space portion 43, a liquid supplying tube 45 is extended along the longitudinal axis C. The liquid supplying tube 45 is made of a resin such as polyether ether ketone (PEEK). In the liquid supplying tube 45, a passage portion 47 is formed. A distal end of the liquid supplying tube 45 is extended to a position which substantially coincides with a position of a distal end of the sheath 41 in the directions parallel to the longitudinal axis C.

Figure 7:
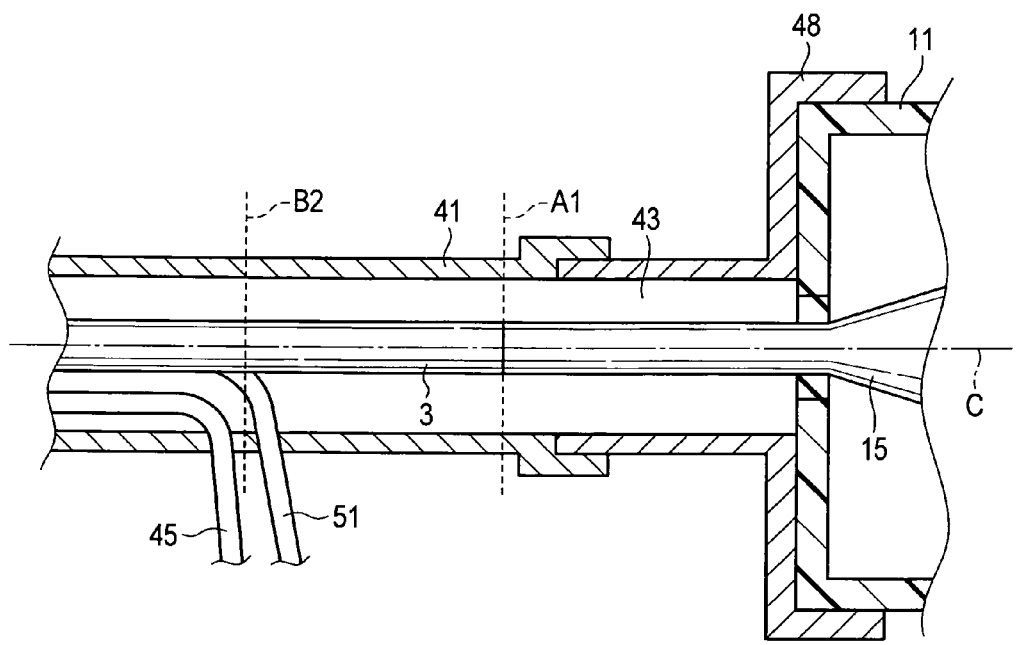
FIG. 7 is a cross-sectional view schematically showing a coupling constitution between the sheath and a vibrator case according to the first embodiment.

FIG. 7 is a view schematically showing a coupling constitution between the sheath 41 and the vibrator case 11. A distal end portion of a cylindrical intermediate member 48 is attached to a proximal end portion of the sheath 41. A distal end portion of the vibrator case 11 is attached to a proximal end portion of the intermediate member 48.

The space portion 43 provided (interposed) between the ultrasonic probe 3 and the sheath 41 is extended to a distal surface of the vibrator case 11. The liquid supplying tube 45 is extended to an outside of the sheath 41 at a part to the distal direction side of the distal of the vibrator case 11. Moreover, as shown in FIG. 1, the liquid supplying tube 45 extends to the outside from the holding case 42, and is connected to a liquid supplying unit 49. The liquid supplying unit 49 is connected to the input unit 10. The liquid supplying unit 49 is driven by input through the input unit 10, or the like, thereby allowing a liquid such as physiological saline to pass through the passage portion 47 of the liquid supplying tube 45. Then, the liquid is supplied (forwarded) to the living tissue or the like from a distal end of the liquid supplying tube (liquid forwarding tube) 45 (a space between the distal end of the sheath 41 and the ultrasonic probe 3).

By supplying the liquid, confirmation of a bleeding spot, washing of a body cavity, or the like is performed. Moreover, in the ultrasonic suction treatment, the ultrasonic vibration is transmitted to the anti-node position at the distal end of the cylindrical member 22 (the vibration transmitting section 20). In this case, by the liquid supplied through the passage portion 47 of the liquid supplying tube 45, the cavitation takes place. Owing to the cavitation, a living tissue of, e.g. hepatic cells having a low elasticity is selectively shattered (crushed) and emulsified. In this case, a living tissue such as the blood vessel having a high elasticity is not shattered by the cavitation.

Figure 8:
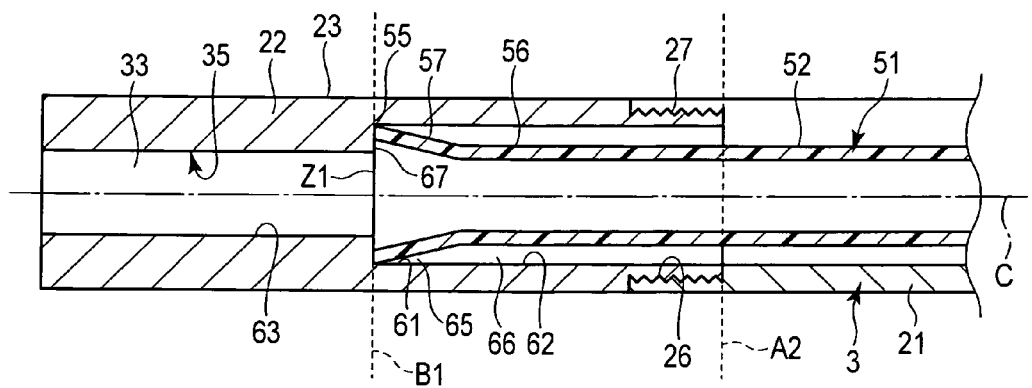
FIG. 8 is a cross-sectional view schematically showing an inner constitution of a cylindrical member of the ultrasonic probe according to the first embodiment.

FIG. 8 is a view showing an inner constitution of the cylindrical member 22 of the ultrasonic probe 3. As shown in FIG. 8, the hole defining portion 35 which defines the hole-shaped portion 33 is extended in the cylindrical member 22 from a distal end to a proximal end. A tube member 51 is inserted into the hole-shaped portion 33 from the proximal direction side. The tube member is made of a resin such as PEEK. Moreover, the tube member 51 is a non-vibrating member configured not to vibrate by the ultrasonic vibration. It is to be noted that the ultrasonic probe 3 and the tube member 51 constitute a probe unit to be attached to the distal direction side of the horn (the amplitude enlarging section) 15.

FIG. 9 is a view showing the cylindrical member 22 and the tube member 51 in a disassembled state. As shown in FIG. 8 and FIG. 9, the tube member 51 includes an outer peripheral portion 52. Moreover, the tube member 51 includes a first tube dimension portion 55 formed by a whole circumference of a tube distal end Z1 around the longitudinal axis C, and a second tube dimension portion 56 provided to the proximal direction side to the first tube dimension portion 55. In the first tube dimension portion 55, a dimension between the longitudinal axis C and the outer peripheral portion 52 of the tube member 51 is a first tube dimension R1. Moreover, in the second tube dimension portion 56, a dimension between the longitudinal axis C and the outer peripheral portion 52 of the tube member 51 is a second tube dimension R2. The second tube dimension R2 is smaller than the first tube dimension R1.

A taper portion 57 is provided (interposed) between the first tube dimension portion 55 and the second tube dimension portion 56. By the taper portion 57, the dimension between the longitudinal axis C and the outer peripheral portion 52 of the tube member 51 changes from the first tube dimension R1 to the second tube dimension R2. That is, the taper portion 57 is a tube dimension change portion configured to change the dimension between the longitudinal axis C and the outer peripheral portion 52 of the tube member 51 from the first tube dimension R1 to the second tube dimension R2. In the taper portion 57, a dimension between the longitudinal axis C and an inner peripheral portion of the tube member 51 also changes in accordance with the change of the dimension between the longitudinal axis C and the outer peripheral portion 52 of the tube member 51.

It is to be noted that the first tube dimension portion 55 and the taper portion 57 are formed by allowing a metal such as soldering iron to abut on the tube member 51. At the formation, a temperature of the metal allowed to abut on the tube member 51 is set to about 300° C. In consequence, the tube member made of the resin softens, and becomes deformable.

As shown in FIG. 8 and FIG. 9, in the cylindrical member 22, a first node position B1 of the ultrasonic vibration is located. The first node position B1 is located between the second anti-node position A2 at the proximal end of the cylindrical member 22 and the anti-node position at the distal end of the cylindrical member 22 in the directions parallel to the longitudinal axis C.

The hole defining portion 35 includes a first hole dimension defining portion 61 including the first node position B1, and a second hole dimension defining portion 62 provided to the proximal direction side of the first hole dimension defining portion 61. A distal end of the first hole dimension defining portion 61 substantially coincides with (matches) the first node position B1 in the directions parallel to the longitudinal axis C. A first hole dimension portion 65 is defined by the first hole dimension defining portion 61, and a second hole dimension portion 66 is defined by the second hole dimension defining portion 62. In the first hole dimension defining portion 61, a dimension between the longitudinal axis C and the hole defining portion 35 is a first hole dimension D1. In the second hole dimension defining portion 62, a dimension between the longitudinal axis C and the hole defining portion 35 is a second hole dimension D2. The first hole dimension D1 is about the same size as the second hole dimension D2.

Moreover, the hole defining portion 35 includes a third hole dimension defining portion 63 extended toward the distal direction from the first node position B1. The third hole dimension defining portion 63 is provided over the whole circumference around the longitudinal axis C, and is extended to the distal end of the cylindrical member 22. In the third hole dimension defining portion 63, a dimension between the longitudinal axis C and the hole defining portion 35 is a third hole dimension D3. The third hole dimension D3 is smaller than the first hole dimension D1 and the second hole dimension D2, and smaller than the first tube dimension R1. Moreover, at the first node position B1, an intermediate surface 67 via which the first hole dimension defining portion 61 is continuous with the third hole dimension defining portion 63 is provided. The intermediate surface 67 is provided substantially perpendicularly to the longitudinal axis C.

As shown in FIG. 8, the tube distal end Z1 of the tube member 51 is connected to the hole defining portion 35 at the first node position B1. That is, at a part to the distal direction side of the horn 15 which is the amplitude enlarging section, the tube distal end Z1 of the tube member 51 is connected to the hole defining portion 35. Here, the third hole dimension D3 is smaller than the first tube dimension R1 in the first tube dimension portion 55 (the tube distal end Z1). Therefore, movement of the tube distal end Z1 toward the distal direction from the first node position B1 is regulated, and the tube distal end Z1 abuts on the intermediate surface 67. Consequently, in the directions parallel to the longitudinal axis C, the tube distal end Z1 of the tube member 51 is disposed at about the same position as the first node position B1.

A class of fit between the first hole dimension portion 65 and the first tube dimension portion 55 is transition fit or close fit. Here, while the class of the fit between the first hole dimension portion 65 and the first tube dimension portion 55 is the close fit, a maximum allowable value of the first hole dimension D1 of the first hole dimension defining portion 61 is smaller than a minimum allowable value of the first tube dimension R1 of the first tube dimension portion 55. Moreover, while the class of the fit between the first hole dimension portion 65 and the first tube dimension portion 55 is the transition fit, a minimum allowable value of the first hole dimension D1 is smaller than a maximum allowable value of the first tube dimension R1, and the minimum allowable value of the first tube dimension R1 is smaller than the maximum allowable value of the first hole dimension D1. Therefore, since the class of the fit between the first hole dimension portion 65 and the first tube dimension portion 55 is the transition fit or the close fit, the first tube dimension portion 55 does not move with respect to the first hole dimension defining portion 61. Therefore, the tube distal end Z1 (the first tube dimension portion 55) is firmly fixed to the hole defining portion 35 at the first node position B1. As described above, the tube distal end Z1 of the tube member 51 is connected to the hole defining portion 35 of the cylindrical member 22 without using any different members other than the cylindrical member 22 and the tube member 51.

Moreover, a class of fit between the second hole dimension portion 66 and the second tube dimension portion 56 is clearance fit. Here, while the class of the fit between the second hole dimension portion 66 and the second tube dimension portion 56 is the clearance fit, a maximum allowable value of the second tube dimension R2 of the second tube dimension portion 56 is smaller than a minimum allowable value of the second hole dimension D2 of the second hole dimension defining portion 62. Therefore, since the class of the fit between the second hole dimension portion 66 and the second tube dimension portion 56 is the clearance fit, a clearance having a sufficiently large size is acquired between the second hole dimension defining portion 62 and the second tube dimension portion 56. Therefore, even while the tube distal end Z1 of the tube member 51 is fixed to the hole defining portion 35, contact of the second tube dimension portion 56 with the second hole dimension defining portion 62 is effectively prevented. In consequence, a contact region between the outer peripheral portion 52 of the tube member 51 and the hole defining portion 35 decreases.

It is to be noted that the class of the fit between the first hole dimension portion 65 and the first tube dimension portion 55 is preferably the transition fit. In this case, the tube member 51 is removed from the cylindrical member 22 by use of a lubricant, a tool or the like, without damaging the cylindrical member 22 and the tube member 51. On the other hand, when the class of the fit between the first hole dimension portion 65 and the first tube dimension portion 55 is the close fit and the tube member 51 is removed from the cylindrical member 22, the cylindrical member 22 or the tube member 51 might be damaged.

FIG. 10 is a view showing an assembled state of the tube member 51 and the probe main body 21. As shown in FIG. 10, the tube member 51 is extended toward the proximal direction from the first node position B1 through the hole-shaped portion 33 and the groove-shaped portion 31. Moreover, the tube member 51 is extended from the groove-shaped portion 31 to the space portion 43 between the ultrasonic probe 3 and the sheath 41. That is, the tube member 51 is extended from the groove-shaped portion 31 to the outside of the probe main body 21 (the vibration transmitting section 20). The tube member 51 is extended from a second node position B2 of the ultrasonic vibration, which is different from the first node position B1, to the outside of the vibration transmitting section 20. The second node position B2 is located between the first anti-node position A1 and the second anti-node position A2. As above, the tube member 51 is bent from the direction parallel to the longitudinal axis C to the first perpendicular direction (the direction of the arrow X1 of FIG. 5) at the second node position B2, and is extended to the outside from the vibration transmitting section 20.

As shown in FIG. 7, the tube member 51 extended out the space portion 43 is extended to the outside of the sheath 41 at a part to the distal direction side of the distal surface of the vibrator case 11. Moreover, as shown in FIG. 1, the tube member 51 is extended to the outside from the holding case 42, and is connected to a suction unit 69. The suction unit 69 is connected to the input unit 10.

When the resected living tissue by the cavitation and liquid are suctioned (sucked), the suction unit 69 is driven by the input through the input unit 10, or the like. When the suction unit 69 is driven, the resected living tissue and liquid are suctioned through the distal end of the hole-shaped portion 33. Then, the living tissue and liquid are suctioned and collected through an inside of the tube member 51 by the suction unit 69. In this case, the tube member 51 is extended to the first node position B1 of the cylindrical member 22 which is located in the distal end portion of the vibration transmitting section 20. Therefore, the greater part of the suction path of the living tissue and liquid is defined by the tube member 51. Therefore, the living tissue and liquid to be suctioned do not easily adhere to the ultrasonic probe 3 (the vibration transmitting section 20).

Next, an action (function) of the ultrasonic treatment device 1 of the present embodiment will be described. When the ultrasonic suction of the living tissue is performed by using the ultrasonic treatment device 1, the current is supplied from the ultrasonic control section 8 to the ultrasonic vibrator 12 through the electric signal lines 13A and 13B, thereby generating the ultrasonic vibration by the ultrasonic vibrator 12. Then, the ultrasonic vibration is transmitted from the proximal end to the distal end of the vibration transmitting section 20 (the ultrasonic probe 3).

Here, at the first anti-node position A1 located at the proximal end of the groove defining portion 32 (the distal end of the horn 15), the cross-sectional shape of the vibration transmitting section 20 which is perpendicular to the ultrasonic vibration transmitting direction and vibrating direction (the longitudinal axis C) changes. That is, the cross-sectional shape of the vibration transmitting section 20 which is perpendicular to the longitudinal axis C changes from the columnar shape which is point symmetrical about (around) the longitudinal axis C to the concaved shape which is not point symmetrical about the longitudinal axis C, at the first anti-node position A1. At the position where the cross-sectional shape of the vibration transmitting section 20 which is perpendicular to the ultrasonic vibration transmitting direction and vibrating direction noticeably changes, the ultrasonic vibration is easily influenced by stress in the directions perpendicular to the longitudinal axis C. Under the influence of the stress, a vibration mode of the ultrasonic vibration changes, and the ultrasonic vibration is not suitably transmitted to the distal end of the ultrasonic probe 3 (the vibration transmitting section 20).

Therefore, the present embodiment is set to the state where the cross-sectional shape of the vibration transmitting section 20 which is perpendicular to the ultrasonic vibration transmitting direction and vibrating direction noticeably changes at the first anti-node position A1. At the anti-node positions of the ultrasonic vibration including the first anti-node position A1, displacement due to the vibration is maximized, but the stress in the directions perpendicular to the longitudinal axis C becomes zero. Therefore, at the first anti-node position A1 where the cross-sectional shape of the vibration transmitting section 20 which is perpendicular to the ultrasonic vibration transmitting direction and vibrating direction noticeably changes, the ultrasonic vibration is not influenced by the stress. Consequently, the vibration mode does not change.

Similarly, the ultrasonic probe 3 is set to the state where the cross-sectional shape of the vibration transmitting section 20 which is perpendicular to the ultrasonic vibration transmitting direction and vibrating direction noticeably changes at the second anti-node position A2 located at the distal end of the groove defining portion 32 (the proximal end of the cylindrical member 22). As described above, at the second anti-node position A2, the displacement due to the vibration is maximized, but the stress in the directions perpendicular to the longitudinal axis C becomes zero. Therefore, at the second anti-node position A2 where the cross-sectional shape of the vibration transmitting section 20 which is perpendicular to the ultrasonic vibration transmitting direction and vibrating direction noticeably changes, the ultrasonic vibration is not influenced by the stress. Consequently, the vibration mode does not change.

As described above, the present embodiment is set to the state where the ultrasonic vibration is not influenced by the stress in the directions perpendicular to the longitudinal axis C, even at the position where the cross-sectional shape of the vibration transmitting section 20 which is perpendicular to the ultrasonic vibration transmitting direction and vibrating direction noticeably changes. Therefore, the ultrasonic vibration is suitably transmitted to the distal end of the ultrasonic probe 3 (the vibration transmitting section 20).

Moreover, the ultrasonic vibration is transmitted to the distal end of the ultrasonic probe 3 (the vibration transmitting section 20) while the liquid is supplied (forwarded) through the passage portion 47 of the liquid supplying tube 45, thereby causing the cavitation. Owing to the cavitation, a living tissue of, e.g. hepatic cells having a low elasticity is selectively shattered and resected. Here, when the cylindrical member 22 is connected to the distal direction side of the probe main body 21, the distal surface of the ultrasonic probe 3 (the vibration transmitting section 20) is formed into a cylindrical shape. For example, when the cylindrical member is not provided, the distal end of the probe main body 21 becomes the distal surface of the ultrasonic probe 3, and hence the distal surface of the ultrasonic probe 3 is formed into a concaved shape. When the distal surface is formed into the cylindrical shape, a surface area of the distal surface of the ultrasonic probe 3 increases as compared with the case where the distal surface is formed into the concaved shape. Since the surface area of the distal surface of the ultrasonic probe 3 increases, the cavitation efficiently takes place, and the living tissue is efficiently and safely shattered and resected. Moreover, the distal end of the ultrasonic probe 3 (the vibration transmitting section 20) is the anti-node position of the ultrasonic vibration, and hence when the ultrasonic vibration is transmitted to the distal end of the cylindrical member 22, the cavitation further efficiently takes place.

Moreover, when the suction unit 69 is driven, the resected living tissue and liquid are suctioned through the distal end of the hole-shaped portion 33 of the cylindrical member 22. Then, the living tissue and liquid are suctioned and collected through the inside of the tube member 51 by the suction unit 69. In this case, the tube member 51 is extended to the first node position B1 of the cylindrical member 22 in the distal end portion of the vibration transmitting section 20. Therefore, the greater part of the suction path of the living tissue and liquid is defined by the tube member 51. Therefore, the living tissue and liquid to be suctioned do not easily adhere to the ultrasonic probe 3 (the vibration transmitting section 20).

Here, as a first comparative example, a vibration transmitting section 20A shown in FIG. 11 is considered. In the vibration transmitting section 20A, an ultrasonic probe 3A is formed into a cylindrical shape from a proximal end to a distal end. Moreover, a hole-shaped portion 33A is defined by a hole defining portion 35A from the distal end of the ultrasonic probe 3A (a distal end of the vibration transmitting section 20A) to a proximal end of an ultrasonic vibrator 12A (a proximal end of the vibration transmitting section 20A) along a longitudinal axis C through an inside of a horn 15A. Moreover, at a node position B3 located to a proximal direction side of the horn 15A which is an amplitude enlarging section, a tube distal end Z2 of a tube member 51A is connected to the hole defining portion 35A. Therefore, a living tissue and liquid to be suctioned by an ultrasonic suction treatment pass through a region (part) of the hole-shaped portion 33A to a distal direction side of the node position B3. That is, in a suction path of the living tissue and liquid, a ratio of the path occupied by a portion defined by the hole defining portion 35A increases. Therefore, the living tissue and liquid to be suctioned and collected easily adhere to the vibration transmitting section 20A (the ultrasonic probe 3A and the horn 15A). When the living tissue and liquid directly adhere to the vibration transmitting section 20A which vibrates by ultrasonic vibration, transmission properties of the ultrasonic vibration deteriorate.

Moreover, in a region to the distal direction side from the horn 15A which is the amplitude enlarging section, an amplitude of the ultrasonic vibration increases, and hence vibration energy increases. Therefore, when the living tissue adheres to the vibration transmitting section 20A in the region to the distal direction side of the horn 15A, a temperature of the living tissue which has adhered is risen by the vibration energy. When the temperature of the living tissue rises, the living tissue hardens owing to a coagulating action (function) of a protein. In consequence, the hardened living tissue is remained in the hole-shaped portion 33A through which the living tissue and liquid to be suctioned pass. When the hardened living tissue is remained in the hole-shaped portion 33A inside the ultrasonic probe 3A, the living tissue and liquid to be suctioned do not easily pass a position where the hardened living tissue is remained. Therefore, in the ultrasonic suction treatment, suction properties of the living tissue and liquid deteriorate.

On the other hand, in the ultrasonic treatment device 1 of the present embodiment, the greater part of the suction path of the living tissue and liquid is defined by the tube member 51. Therefore, the living tissue and liquid to be suctioned (sucked) do not easily adhere to the ultrasonic probe 3 (the vibration transmitting section 20). In consequence, the deterioration of the transmission properties of the ultrasonic vibration, which is caused by the adhesion of the living tissue and liquid to the vibration transmitting section 20, is effectively prevented. Moreover, the deterioration of the suction properties of the living tissue and liquid, which is caused by the adhesion of the living tissue and liquid to the vibration transmitting section 20, is also effectively prevented.

Moreover, when the ultrasonic probe 3 is formed, the probe main body 21 and the cylindrical member 22 are formed. In the ultrasonic probe 3, the probe main body 21 provided with the groove-shaped portion 31 occupies the greater part of the dimension of the ultrasonic probe 3 along the longitudinal axis C. The probe main body 21 is formed into the concaved shape from the proximal end to the distal end. Furthermore, when the cylindrical member 22 is connected to the distal direction side of the probe main body 21, the ultrasonic probe 3 is formed.

Figure 12:
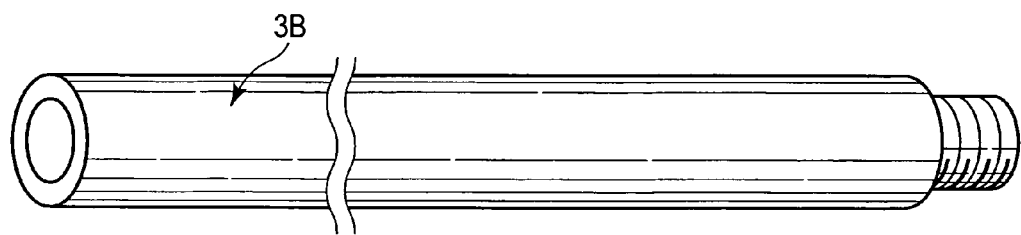
FIG. 12 is a perspective view schematically showing an ultrasonic probe according to a second comparative example.

Here, as a second comparative example, an ultrasonic probe 3B is considered as shown in FIG. 12. The ultrasonic probe 3B is formed into a cylindrical shape from a distal end to a proximal end along a longitudinal axis C. The ultrasonic probe 3B is formed by subjecting a columnar member (not shown) punching (drilling). Here, the columnar member which is a material of the ultrasonic probe 3B has a large dimension along the longitudinal axis C, and a small dimension in directions perpendicular to the longitudinal axis C. The punching of such an elongate columnar member is performed for a long period of time by use of a drill for exclusive use, which increases cost.

On the other hand, the concaved probe main body 21 is formed for a shorter period of time at lower cost as compared with the punching of the columnar member. Moreover, a dimension of the cylindrical member 22 which requires the punching along the longitudinal axis C is small. Therefore, a time required for the punching is short as compared with a case where the ultrasonic probe 3B is formed. Therefore, the ultrasonic probe 3 is efficiently manufactured at low cost.

Moreover, when the tube member 51 is attached to the ultrasonic probe 3, the tube member is inserted into the groove-shaped portion 31 from the outside of the ultrasonic probe 3 (the vibration transmitting section 20). Then, the tube member is inserted into the hole-shaped portion 33 from the groove-shaped portion 31, and the tube distal end Z1 of the tube member 51 is connected to the hole defining portion 35 of the cylindrical member 22 at the first node position B1.

Here, the tube member 51 is inserted into the groove-shaped portion 31 from the second node position B2 between the first anti-node position A1 and the second anti-node position A2. Therefore, while the tube member 51 is attached to the ultrasonic probe 3, the tube member 51 is bent from the direction parallel to the longitudinal axis C to the first perpendicular direction (the direction of the arrow X1 of FIG. 5) at the second node position B2, to be extended to the outside from the vibration transmitting section 20. At the node positions of the ultrasonic vibration including the second node position B2, the stress in the directions perpendicular to the longitudinal axis C is maximized, but the displacement due to the ultrasonic vibration becomes zero. Therefore, even when the tube member 51 is bent at the second node position B2, a bent portion of the tube member 51 is not easily influenced by the ultrasonic vibration. In consequence, the tube member 51 is effectively prevented from being damaged.

Moreover, the tube distal end Z1 of the tube member 51 is connected to the hole defining portion 35 of the cylindrical member 22 at the first node position B1. As described above, at the node position of the ultrasonic vibration, the stress in the directions perpendicular to the longitudinal axis C is maximized, but the displacement due to the vibration becomes zero. Therefore, even when the vibration transmitting section 20 (the ultrasonic probe 3) ultrasonically vibrates, the tube member 51 is firmly fixed to the hole defining portion 35.

Here, there is considered a case where the tube member 51 is attached to the ultrasonic probe 3B of the second comparative example (see FIG. 12). In the cylindrical ultrasonic probe 3B, the tube member 51 is not easily moved. Therefore, the tube member 51 is not easily moved from the proximal direction side through the inside of the ultrasonic probe 3B until the tube distal end Z1 of the tube member 51 is positioned in the distal end portion of the ultrasonic probe 3B. Therefore, operability in attaching the tube member 51 to the ultrasonic probe 3B deteriorates.

On the other hand, in the present embodiment, the tube member 51 is inserted into the groove-shaped portion 31 of the concaved probe main body 21, and the tube member 51 moves along the groove-shaped portion 31. In the groove-shaped portion 31, the tube member 51 easily moves as compared with the inside of the cylindrical ultrasonic probe 3B. Moreover, a dimension along the longitudinal axis C from the proximal end of the hole-shaped portion 33 of the cylindrical member 22 to the first node position B1 through which the tube member 51 does not easily move is small. Therefore, as compared with the case where the tube member 51 is attached to the ultrasonic probe 3B, the tube member 51 is easily attached to the ultrasonic probe 3.

Moreover, the class of the fit between the first hole dimension portion 65 of the ultrasonic probe 3 and the first tube dimension portion 55 is the transition fit or the close fit. Therefore, the first tube dimension portion 55 does not move with respect to the first hole dimension defining portion 61. Therefore, the tube distal end Z1 (the first tube dimension portion 55) is firmly fixed to the hole defining portion 35 at the first node position B1. As described above, the tube distal end Z1 of the tube member 51 is connected to the hole defining portion 35 of the cylindrical member 22 without using any different members other than the cylindrical member 22 and the tube member 51. Since any different (separate) members are not used to connect the tube distal end Z1 of the tube member 51 to the cylindrical member 22 (the ultrasonic probe 3), a constitution of the ultrasonic probe 3 is simplified, and manufacturing cost of the ultrasonic probe 3 decreases.

Furthermore, the class of the fit between the second hole dimension portion 66 and the second tube dimension portion 56 is the clearance fit. Therefore, the clearance having a sufficiently large size is acquired between the second hole dimension defining portion 62 and the second tube dimension portion 56. Consequently, even while the tube distal end Z1 of the tube member 51 is fixed to the hole defining portion 35, the contact of the second tube dimension portion 56 with the second hole dimension defining portion 62 is effectively prevented. In consequence, the contact region between the outer peripheral portion 52 of the tube member 51 and the hole defining portion 35 decreases. Therefore, when the vibration transmitting section 20 ultrasonically vibrates, friction between the hole defining portion 35 of the vibration transmitting section 20 (the cylindrical member 22) and the tube member 51 which is the non-vibrating member decreases. In consequence, heat generation between the hole defining portion 35 of the vibration transmitting section 20 and the tube member 51 is effectively prevented.

Additionally, the third hole dimension D3 in the hole defining portion 35 is smaller than the first tube dimension R1 in the first tube dimension portion 55 (the tube distal end Z1) of the tube member 51. Therefore, the movement of the tube distal end Z1 toward the distal direction from the first node position B1 is regulated, and the tube distal end Z1 abuts on the intermediate surface 67. Consequently, in the directions parallel to the longitudinal axis C, the tube distal end Z1 of the tube member 51 is suitably disposed at about the same position as the first node position B1.

In consequence, the ultrasonic treatment device 1 of the above constitution produces the following effect. That is, in the ultrasonic treatment device 1, the tube member 51 is extended up to the first node position B1 of the cylindrical member 22 which is located in the distal end portion of the vibration transmitting section 20. Thus, the greater part of the suction path of the living tissue and liquid is defined by the tube member 51. Therefore, the living tissue and liquid to be suctioned and collected do not easily adhere to the ultrasonic probe 3 (the vibration transmitting section 20). In consequence, it is possible to effectively prevent the deterioration of the transmission properties of the ultrasonic vibration caused by the adhesion of the living tissue and liquid to the vibration transmitting section 20. Moreover, it is also possible to effectively prevent the deterioration of the suction properties of the living tissue and liquid caused by the adhesion of the living tissue and liquid to the vibration transmitting section 20.

Moreover, in the ultrasonic probe 3, the class of the fit between the first hole dimension portion 65 and the first tube dimension portion 55 is the transition fit or the close fit. Therefore, the first tube dimension portion 55 does not move with respect to the first hole dimension defining portion 61. In consequence, the tube distal end Z1 (the first tube dimension portion 55) can firmly be fixed to the hole defining portion 35 at the first node position B1. Furthermore, since the tube distal end Z1 is fixed as described above, the tube distal end Z1 of the tube member 51 is connected to the hole defining portion 35 of the cylindrical member 22 without using any different members other than the cylindrical member 22 and the tube member 51. Since any different (separate) members are not used to connect the tube distal end Z1 of the tube member 51 to the cylindrical member 22 (the ultrasonic probe 3), it is possible to realize the simplification of the constitution of the ultrasonic probe 3 and the decrease of the manufacturing cost of the ultrasonic probe 3.

Furthermore, the class of the fit between the second hole dimension portion 66 and the second tube dimension portion 56 is the clearance fit. Therefore, the clearance having a sufficiently large size is acquired between the second hole dimension defining portion 62 and the second tube dimension portion 56. Consequently, even while the tube distal end Z1 of the tube member 51 is fixed to the hole defining portion 35, the contact of the second tube dimension portion 56 with the second hole dimension defining portion 62 is effectively prevented. In consequence, the contact region between the outer peripheral portion 52 of the tube member 51 and the hole defining portion 35 decreases. Therefore, when the vibration transmitting section 20 ultrasonically vibrates, the friction between the hole defining portion 35 of the vibration transmitting section 20 (the cylindrical member 22) and the tube member 51 which is the non-vibrating member decreases. In consequence, the heat generation between the hole defining portion 35 of the vibration transmitting section 20 and the tube member 51 can effectively be prevented.

(Modification of First Embodiment)

Figure 13:
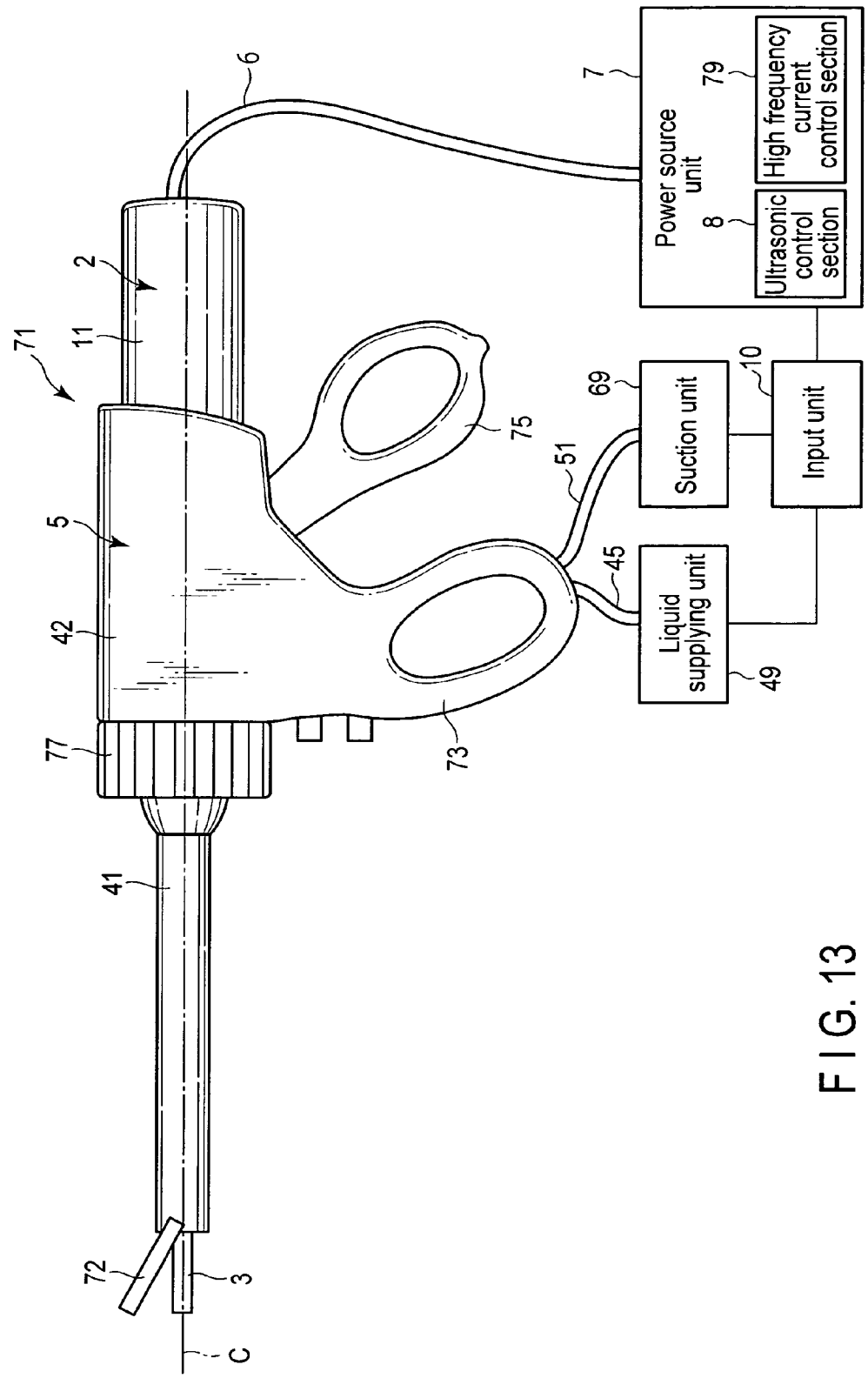
FIG. 13 is a schematic view showing an ultrasonic treatment device according to a first modification of the first embodiment.

It is to be noted that in the first embodiment, the ultrasonic treatment device 1 performs only the ultrasonic suction, in which the living tissue is selectively shattered and resected by the cavitation caused by the ultrasonic vibration and the resected living tissue is suctioned, but the present invention is not limited to this embodiment. For example, as a first modification shown in FIG. 13, coagulation-and-cutting of a living tissue such as a blood vessel grasped between an ultrasonic probe 3 and a jaw 72 may be performed by an ultrasonic treatment device 71. In the ultrasonic treatment device 71, a fixed handle 73 is provided integrally with a holding case 42. Moreover, a movable handle 75 openable/closable to the fixed handle 73 is provided. Furthermore, the jaw 72 is attached to a distal end portion of a sheath 41. When the movable handle 75 is opened and closed with respect to the fixed handle 73, a movable member (not shown) provided in the sheath 41 moves along a longitudinal axis C. In consequence, the jaw 72 performs an opening/closing motion with respect to a distal end portion of the ultrasonic probe 3.

Furthermore, a rotary operation knob 77 is coupled with the holding case 42. The rotary operation knob 77 is rotatable with respect to the holding case 42 around the longitudinal axis C. The sheath 41 is attached to an inner peripheral direction side of the rotary operation knob 77. When the rotary operation knob 77 is rotated, the ultrasonic probe 3 and the sheath 41 rotate together with the rotary operation knob 77 around the longitudinal axis C.

Furthermore, a liquid supplying tube 45 and a tube member 51 extended to the outside from the sheath 41 pass through the fixed handle 73. Then, the liquid supplying tube 45 and the tube member 51 is extended to the outside of the fixed handle 73 from an end of the fixed handle 73 on a side opposite to the holding case 42.

Additionally, in the ultrasonic treatment device 71, a power source unit 7 includes a high frequency current control section 79. An electric signal line (not shown) extended through an inside of a cable 6 from the high frequency current control section 79 of the power source unit 7 is connected to the ultrasonic vibrator 12, the electric signal line being different (separately) from the electric signal lines 13A and 13B. In consequence, a probe side current path of a high frequency current is formed from the high frequency current control section 79 to the distal end portion of the ultrasonic probe 3 through an ultrasonic vibrator 12 and a horn 15. Moreover, an electric signal line (not shown) extended through the inside of the cable 6 from the high frequency current control section 79 of the power source unit 7 is connected to a vibrator case 11. The vibrator case 11 and an intermediate member 48 include conductive portions (not shown) which electrically connect the sheath 41 to the electric signal line from the high frequency current control section 79. In consequence, a jaw side current path of the high frequency current is formed from the high frequency current control section 79 to the jaw 72 through the conductive portion of the vibrator case 11 and the sheath 41. It is to be noted that the ultrasonic vibrator 12 and the horn 15 are insulated from the vibrator case 11. Similarly, the sheath 41 is insulated from the ultrasonic probe 3.

Between the jaw 72 and the distal end portion of the ultrasonic probe 3, the living tissue having the high elasticity, for example, the blood vessel or the like which is not shattered by the cavitation is treated. By ultrasonically vibrating the ultrasonic probe 3, friction heat is generated between the ultrasonic probe 3 and the living tissue. The living tissue is cut (incised) by the generated friction heat. Moreover, when the high frequency current flows through the living tissue between the jaw 72 and the distal end portion of the ultrasonic probe 3, the living tissue is reformed. In consequence, the living tissue is coagulated.

As seen from the above, the ultrasonic treatment device (1 or 71) may include a treatment function (surgery function) other than the ultrasonic suction of selectively shattering and resecting the living tissue by the cavitation caused by the ultrasonic vibration and suctioning the resected living tissue.

Moreover, in the first embodiment, the probe main body 21 (the ultrasonic probe 3) is provided with the groove-shaped portion 31 recessed from the first perpendicular direction (the direction of the arrow X1 of FIG. 5), which is perpendicular to the longitudinal axis C, to the second perpendicular direction (the direction of the arrow X2 of FIG. 5), but the present invention is not limited to this embodiment. For example, as a second modification shown in FIG. 14 and FIG. 15, a through hole 81 extended through a probe main body 21 from a first perpendicular direction (a direction of an arrow X1 of FIG. 15) to a second perpendicular direction (a direction of an arrow X2 of FIG. 15) may be defined in the probe main body 21 (a vibration transmitting section 20) by a through hole defining portion 82.

While a horn 15 and a cylindrical member 22 are coupled with the probe main body 21, the through hole 81 is defined from a first anti-node position A1 of ultrasonic vibration to a second anti-node position A2 of the ultrasonic vibration which is different from the first anti-node position A1, along a longitudinal axis C by the through hole defining portion 82. A first perpendicular direction side end and a second perpendicular direction side end of the through hole defining portion 82 are continuous with an outer peripheral portion 23 of an ultrasonic probe 3. According to the above constitution, a cross-sectional shape of a vibration transmitting section 20 which is perpendicular to the longitudinal axis C changes from a columnar shape which is point symmetrical about the longitudinal axis C to a shape which is not point symmetrical about the longitudinal axis C, at the first anti-node position A1. Similarly, the cross-sectional shape of the vibration transmitting section 20 which is perpendicular to the longitudinal axis C changes from the shape which is not point symmetrical about the longitudinal axis C to a cylindrical shape which is point symmetrical about the longitudinal axis C, at the second anti-node position A2.

While the cylindrical member 22 is connected to the probe main body 21, a tip of the through orifice 81 communicates with an orifice 33. A tube member 51 having a tube tip Z1 connected to an orifice regulating portion 35 of the cylindrical member 22 at a first node position B1 passes through the orifice 33 to extend along the longitudinal axis C toward the through orifice 81. Then, the tube member 51 is extended through the through hole 81 to the outside from the probe main body 21 (the vibration transmitting section 20). Here, the tube member 51 is extended from a second node position B2 between the first anti-node position A1 and the second anti-node position A2 to the outside of the probe main body 21.

As seen from the above first embodiment and the second modification of the first embodiment, the probe main body 21 (the vibration transmitting section 20) may include a void defining portion (32, 82) which defines a void portion (31, 81) extended from the first perpendicular direction to the second perpendicular direction, these directions being perpendicular to the longitudinal axis C. Moreover, while the horn 15 and the cylindrical member 22 are coupled with the probe main body 21, the void portion (31, 81) may be defined along the longitudinal axis C from the first anti-node position A1 of the ultrasonic vibration to the second anti-node position A2 of the ultrasonic vibration which is different from the first anti-node position A1, by the void defining portion (32, 82). Moreover, at least a first perpendicular direction (the direction of the arrow X1 in FIG. 5 or FIG. 15) side end of the void defining portion (32, 82) may be continuous with the outer peripheral portion 23 of the ultrasonic probe.

Moreover, a distal end of the void portion (31, 81) may communicate with the hole-shaped portion 33 of the cylindrical member 22 (the vibration transmitting section 20). Furthermore, the tube member 51, having the tube distal end Z1 connected to the hole defining portion 35 of the cylindrical member 22 at the first node position B1, may pass through the hole-shaped portion 33 and the void portion (31, 81) and may be extended from the void portion (31 or 81) to the outside of the probe main body 21 (the vibration transmitting section 20). According to the above constitution, the ultrasonic probe 3 is efficiently manufactured at low cost as described above in the first embodiment. Moreover, the tube member 51 is easily attached to the ultrasonic probe 3.

Figure 16:
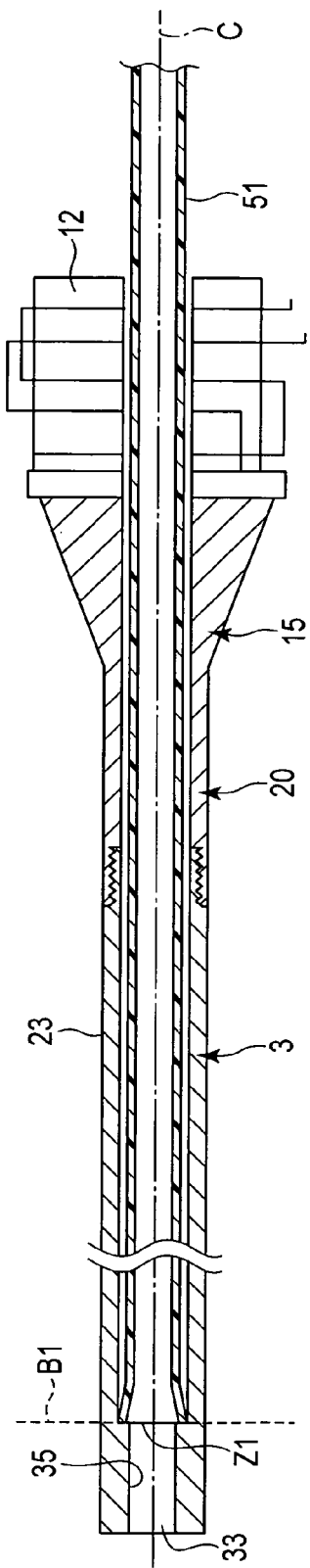
FIG. 16 is a cross-sectional view schematically showing a vibration transmitting section according to a third modification of the first embodiment.

Furthermore, from the viewpoint of preventing the adhesion of the living tissue and liquid to be suctioned to the vibration transmitting section 20, it is not necessary to form void portions such as the groove-shaped portion 31 and the through hole 81 in the ultrasonic probe 3. For example, as a third modification shown in FIG. 16, a vibration transmitting section 20 does not have to include the void portion (31, 81). According to the present modification, in the vibration transmitting section 20 from a distal end to a proximal end, a hole-shaped portion 33 is defined along a longitudinal axis C by a hole defining portion 35. A tube distal end Z1 of a tube member 51 is connected to the hole defining portion 35 at a first node position B1 located in a distal end portion of an ultrasonic probe 3. That is, the tube distal end Z1 of the tube member 51 is connected to the hole defining portion 35 at the first node position B1 to a distal direction side of a horn 15 which is an amplitude enlarging section. The tube member 51 passes through the hole-shaped portion 33 and is extended from a proximal end of an ultrasonic vibrator 12 (a proximal end of the vibration transmitting section 20) to the outside of the vibration transmitting section 20. Then, the tube member is extended to the outside of the vibrator case 11, and is connected to a suction unit 69.

Also in the present modification, similarly to the first embodiment, the greater part of the suction path of the living tissue and liquid is defined by the tube member 51. Therefore, the living tissue and liquid to be suctioned do not easily adhere to the ultrasonic probe 3 (the vibration transmitting section 20). However, the tube member 51 is not easily moved in the hole-shaped portion 33 as compared with void portions such as the groove-shaped portion 31 and the through hole 81. Therefore, the tube member 51 is not easily moved inside the vibration transmitting section 20 from the proximal direction side until the tube distal end Z1 of the tube member 51 is positioned in the distal end portion of the ultrasonic probe 3. In consequence, as compared with the first embodiment, operability in attaching the tube member 51 to the ultrasonic probe 3 (the vibration transmitting section 20) deteriorates.

Figure 17:
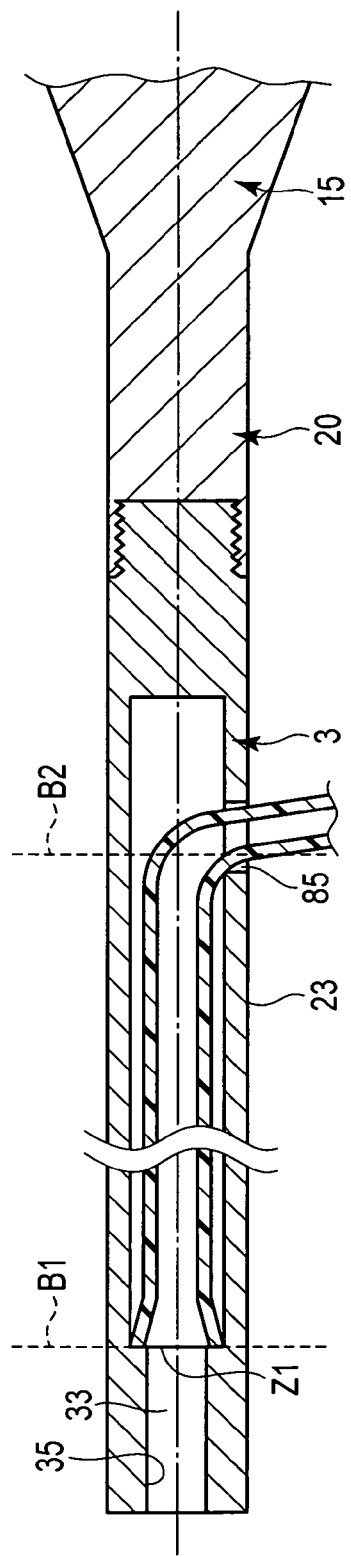
FIG. 17 is a cross-sectional view schematically showing a vibration transmitting section according to a fourth modification of the first embodiment.

Moreover, as a constitution where the vibration transmitting section 20 is not provided with the void portion (31, 81), a fourth modification shown in FIG. 17 is also considered. According to the present modification, in an ultrasonic probe 3, a hole-shaped portion 33 is defined by a hole defining portion 35. A proximal end of the hole-shaped portion 33 is positioned to a distal direction side of a horn 15 which is an amplitude enlarging section. In a part to a proximal direction side of the proximal end of the hole-shaped portion 33, a vibration transmitting section 20 is formed into a columnar shape. Therefore, an ultrasonic vibrator 12 and the horn 15 are formed into the columnar shape. A tube distal end Z1 of a tube member 51 is connected to the hole defining portion 35 at a first node position B1 located in a distal end portion of the ultrasonic probe 3. That is, the tube distal end Z1 of the tube member 51 is connected to the hole defining portion 35 at the first node position B1 to the distal direction side of the horn 15 which is the amplitude enlarging section.

Furthermore, at a second node position B2 of the ultrasonic probe 3, a through port 85 extended through the ultrasonic probe 3 from an outer peripheral portion 23 of the ultrasonic probe 3 to the hole-shaped portion 33 is provided. The second node position B2 is located to the distal direction side of the proximal end of the hole-shaped portion 33. The tube member 51 passes through the hole-shaped portion 33, and is bent from a direction parallel to a longitudinal axis C to a direction perpendicular to the longitudinal axis C at the second node position B2. Then, the tube member passes through the through port 85 from the second node position B2, and is extended to the outside of the vibration transmitting section 20. At the second node position B2, stress in the directions perpendicular to the longitudinal axis C is maximized, but displacement due to ultrasonic vibration becomes zero. Therefore, also when the tube member 51 is bent at the second node position B2, a bent portion of the tube member 51 is not easily influenced by the ultrasonic vibration. Therefore, the tube member 51 is effectively prevented from being damaged.

Also in the present modification, similarly to the first embodiment, the greater part of the suction path of the living tissue and liquid is defined by the tube member 51. Therefore, the living tissue and liquid to be suctioned do not easily adhere to the ultrasonic probe 3 (the vibration transmitting section 20). Moreover, since the through port 85 is provided, a dimension by which the tube member 51 moves through the hole-shaped portion 33 in the directions parallel to the longitudinal axis C decreases, when attaching the tube member 51 to the ultrasonic probe 3. Therefore, the tube member 51 is easily attached to the ultrasonic probe 3 (the vibration transmitting section 20).

However, in the present modification, since the through port 85 is provided, the cross-sectional shape of the vibration transmitting section 20 which is perpendicular to the ultrasonic vibration transmitting direction and vibrating direction noticeably changes at the second node position B2. In consequence, at the second node position B2, the ultrasonic vibration is easily influenced by the stress in the direction perpendiculars to the longitudinal axis C. At the second node position B2, the stress in the directions perpendicular to the longitudinal axis C is maximized. Therefore, under the influence of the stress at the second node position B2, the transmission properties of the ultrasonic vibration deteriorate as compared with the first embodiment.

Figure 18:
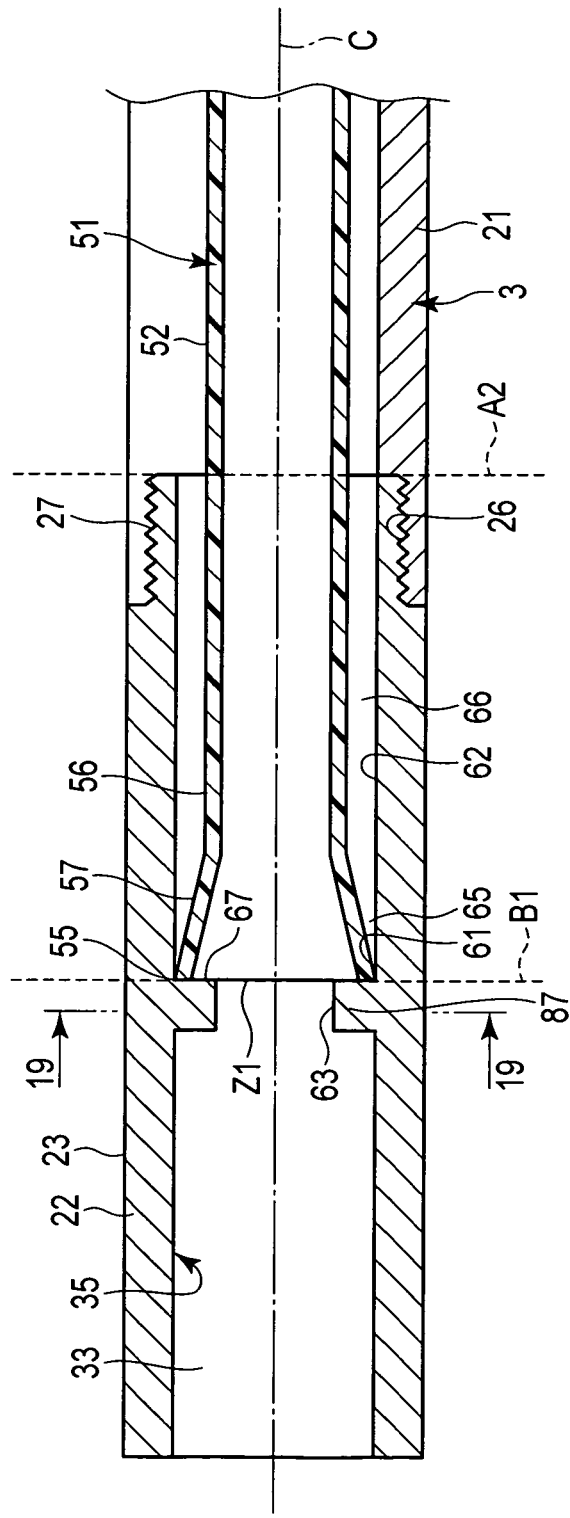
FIG. 18 is a cross-sectional view schematically showing an inner constitution of a cylindrical member of an ultrasonic probe according to a fifth modification of the first embodiment.

Moreover, in the first embodiment, the third hole dimension defining portion 63 is extended up to the distal end of the cylindrical member 22 (the vibration transmitting section 20), but the present invention is not limited to this embodiment. For example, as a fifth modification shown in FIG. 18 and FIG. 19, a projecting portion 87 projecting toward an inner peripheral direction from a first hole dimension defining portion 61 may be provided with a third hole dimension defining portion 63. In the present modification, a projecting end of the projecting portion 87 is the third hole dimension defining portion 63. In the third hole dimension defining portion 63, similarly to the first embodiment, a third hole dimension D3 between a longitudinal axis C and a hole defining portion 35 is smaller than a first hole dimension D1 and a second hole dimension D2, and smaller than a first tube dimension R1.

Furthermore, the projecting portion 87 is provided with an intermediate surface 67 via which the first hole dimension defining portion 61 is continuous with the third hole dimension defining portion 63 at a first node position B1. By the intermediate surface 67, movement of a tube distal end Z1 toward the distal direction from the first node position B1 is regulated, and the tube distal end Z1 abuts on the intermediate surface 67. Consequently, in directions parallel to the longitudinal axis C, the tube distal end Z1 of a tube member 51 is disposed at about the same position as the first node position B1.

Moreover, in the fifth modification, the projecting portion 87 is provided over the whole circumference around the longitudinal axis C, but the present invention is not limited to this modification. For example, as a sixth modification shown in FIG. 20, two projecting portions 87 may be provided apart from each other around a longitudinal axis C. In consequence, a third hole dimension defining portion 63 extended toward the distal direction from a first node position B1 is provided in at least a part (portion) around the longitudinal axis C.

Furthermore, as a seventh modification shown in FIG. 21, the third hole dimension defining portion 63 and the intermediate surface 67 do not have to be provided. Also in the present modification, a tube distal end Z1 of a tube member 51 is connected to a hole defining portion 35 at a first node position B1. Moreover, in a first hole dimension defining portion 61, a class of fit between a first hole dimension portion 65 and a first tube dimension portion 55 is transition fit or close fit. Furthermore, a class of fit between a second hole dimension portion 66 and a second tube dimension portion 56 is clearance fit. However, in the present embodiment, the intermediate surface 67 is not provided. Therefore, when the tube distal end Z1 of the tube member 51 is disposed at about the same position as the first node position B1 in directions parallel to a longitudinal axis C, positioning precision of the tube distal end Z1 deteriorates as compared with the first embodiment.

Additionally, in the first embodiment, the whole circumference of the tube distal end Z1 around the longitudinal axis C is the first tube dimension portion 55, but the present invention is not limited to this embodiment. For example, as an eighth modification shown in FIG. 22, a first tube dimension portion 55 may be extended toward a proximal direction from a tube distal Z1. A second tube dimension portion 56 is provided to a proximal direction side of the first tube dimension portion 55, similarly to the first embodiment. Moreover, a second tube dimension R2 is smaller than a first tube dimension R1. Furthermore, between the first tube dimension portion 55 and the second tube dimension portion 56, a taper portion 57 which is a tube dimension change portion is provided (interposed).

Moreover, in the first embodiment, the dimension between the longitudinal axis C and the inner peripheral portion of the tube member 51 also changes in the taper portion 57, in accordance with the change of the dimension between the longitudinal axis C and the outer peripheral portion 52 of the tube member 51, but the present invention is not limited to this embodiment. For example, as a ninth modification shown in FIG. 23, a dimension between a longitudinal axis C and an inner peripheral portion of a tube member 51 may be unchanged (predetermined) in a taper portion 57. Also in a tenth modification shown in FIG. 24, similarly to the ninth modification, a dimension between a longitudinal axis C and an inner peripheral portion of a tube member 51 may be unchanged (predetermined) in a taper portion 57.

Furthermore, as an eleventh modification shown in FIG. 25, the taper portion 57 does not have to be provided. Instead, a perpendicular surface portion 89 perpendicular to a longitudinal axis C is provided (interposed) between a first tube dimension portion 55 and a second tube dimension portion 56. In the present modification, the perpendicular surface portion 89 is a tube dimension change portion configured to change a dimension between the longitudinal axis C and an outer peripheral portion 52 of a tube member 51 from a first tube dimension R1 to a second tube dimension R2.

As understood from the eighth modification to the eleventh modification of the first embodiment, the first tube dimension portion 55 including the tube distal end Z1 may have the first tube dimension R1, and the second tube dimension portion 56 may have the second tube dimension R2 smaller than the first tube dimension R1. Moreover, between the first tube dimension portion 55 and the second tube dimension portion 56, the tube dimension change portion (57, 89) configured to change the dimension between the longitudinal axis C and the outer peripheral portion 52 of the tube member 51 from the first tube dimension R1 to the second tube dimension R2 may be provided. Furthermore, in the first hole dimension defining portion 61, the class of the fit between the first hole dimension portion 65 and the first tube dimension portion 55 may be the transition fit or the close fit. Additionally, in the second hole dimension defining portion 62, the class of the fit between the second hole dimension portion 66 and the second tube dimension portion 56 may be the clearance fit.

According to the above constitution, as described above in the first embodiment, the tube distal end Z1 of the tube member 51 is connected to the hole defining portion 35 of the cylindrical member 22 without using any different (separate) members other than the cylindrical member 22 and the tube member 51. Moreover, even while the tube distal end Z1 of the tube member 51 is fixed to the hole defining portion 35, the contact of the second tube dimension portion 56 with the second hole dimension defining portion 62 is effectively prevented. In consequence, the contact region between the outer peripheral portion 52 of the tube member 51 and the hole defining portion 35 decreases.

(Second Embodiment)

Next, a second embodiment of the present invention will be described with reference to FIG. 26 and FIG. 27. In the second embodiment, the constitution of the first embodiment is modified as follows. It is to be noted that a constitution common to the first embodiment is denoted with the same reference marks, and description of the constitution is omitted.

FIG. 26 is a view showing an inner constitution of a cylindrical member 22 of an ultrasonic probe 3. As shown in FIG. 26, a hole defining portion 35 which defines a hole-shaped portion 33 is extended in the cylindrical member 22 from a distal end to a proximal end, similarly to the first embodiment. A tube member 51 is inserted into the hole-shaped portion from a proximal direction side.

Figure 27:
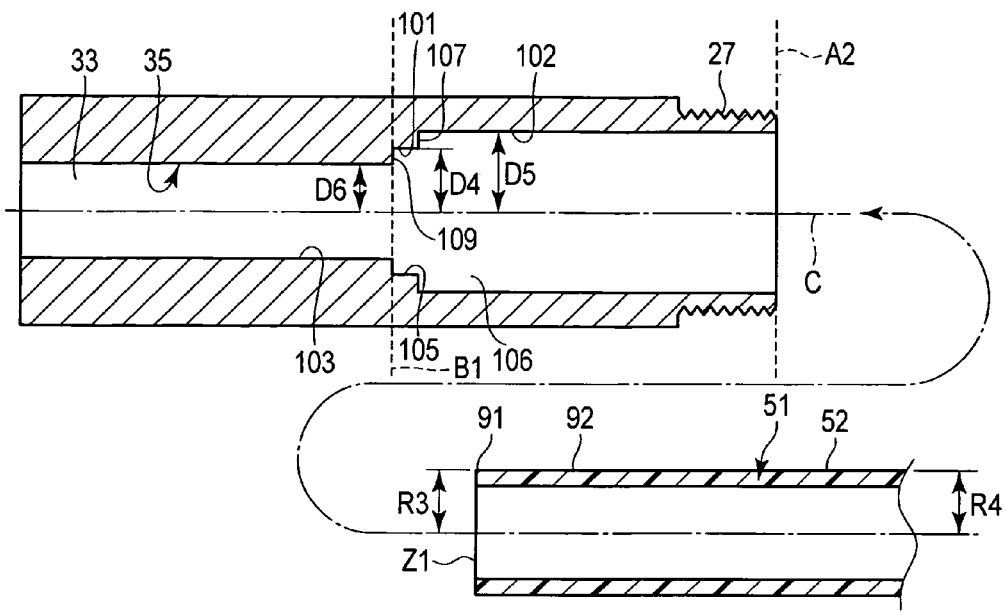
FIG. 27 is a cross-sectional view schematically showing the cylindrical member of the ultrasonic probe and a tube member according to the second embodiment in a disassembled state.

FIG. 27 is a view showing the cylindrical member 22 and the tube member 51 in a disassembled state. As shown in FIG. 26 and FIG. 27, the tube member 51 includes a first tube dimension portion 91 including a tube distal end Z1, and a second tube dimension portion 92 provided to the proximal direction side of the first tube dimension portion 91. In the first tube dimension portion 91, a dimension between a longitudinal axis C and an outer peripheral portion 52 of the tube member 51 is a first tube dimension R3. Moreover, in the second tube dimension portion 92, a dimension between the longitudinal axis C and the outer peripheral portion 52 of the tube member 51 is a second tube dimension R4. In the present embodiment, the first tube dimension R3 is about the same size as the second tube dimension R4. That is, the tube member is provide in a state that the dimension between the longitudinal axis C and the outer peripheral portion 52 is the same from the first tube dimension portion 91 to the second tube dimension portion 92. Therefore, in the present embodiment, the tube member 51 is not provided with a tube dimension change portion such as the taper portion 57.

As shown in FIG. 26 and FIG. 27, in the cylindrical member 22, a first node position B1 of ultrasonic vibration is located. The first node position B1 is located between a second anti-node position A2 of a proximal end of the cylindrical member 22 and an anti-node position at a distal end of the cylindrical member 22 in the directions parallel to the longitudinal axis C.

The hole defining portion 35 includes a first hole dimension defining portion 101 including the first node position B1, and a second hole dimension defining portion 102 provided to the proximal direction side of the first hole dimension defining portion 101. In directions parallel to the longitudinal axis C, a distal end of the first hole dimension defining portion 101 substantially coincides with (matches) the first node position B1. A first hole dimension portion 105 is defined by the first hole dimension defining portion 101, and a second hole dimension portion 106 is defined by the second hole dimension defining portion 102. In the first hole dimension defining portion 101, a dimension between the longitudinal axis C and the hole defining portion 35 is a first hole dimension D4. In the second hole dimension defining portion 102, a dimension between the longitudinal axis C and the hole defining portion 35 is a second hole dimension D5. The second hole dimension D5 is larger than the first hole dimension D4.

Between the first hole dimension defining portion 101 and the second hole dimension defining portion 102, a perpendicular surface 107 perpendicular to the longitudinal axis C is provided (interposed). By the perpendicular surface 107, the dimension between the longitudinal axis C and the hole defining portion 35 changes from the first hole dimension D4 to the second hole dimension D5. That is, the perpendicular surface 107 is a hole dimension change portion configured to change the dimension between the longitudinal axis C and the hole defining portion 35 from the first hole dimension D4 to the second hole dimension D5.

Moreover, the hole defining portion 35 includes a third hole dimension defining portion 103 extended toward the distal direction from the first node position B1. The third hole dimension defining portion 103 is provided over the whole circumference around the longitudinal axis C, and is extended up to the distal end of the cylindrical member 22. In the third hole dimension defining portion 103, a dimension between the longitudinal axis C and the hole defining portion 35 is a third hole dimension D6. The third hole dimension D6 is smaller than the first hole dimension D4, and smaller than the first tube dimension R3 and the second tube dimension R4. Furthermore, at the first node position B1, an intermediate surface 109, via which the first hole dimension defining portion 101 is continuous with the third hole dimension defining portion 103, is provided. The intermediate surface 109 is provided substantially perpendicularly to the longitudinal axis C.

As shown in FIG. 8, the tube distal end Z1 of the tube member 51 is connected to the hole defining portion 35 at the first node position B1. That is, the tube distal end Z1 of the tube member 51 is connected to the hole defining portion 35 to a distal direction side of a horn 15 which is an amplitude enlarging section. Here, the third hole dimension D6 is smaller than the first tube dimension R3 in the first tube dimension portion 91 (the tube distal end Z1). Therefore, movement of the tube distal end Z1 toward the distal direction from the first node position B1 is regulated, and the tube distal end Z1 abuts on the intermediate surface 109. Consequently, in directions parallel to the longitudinal axis C, the tube distal end Z1 of the tube member 51 is disposed at about the same position as the first node position B1.

A class of fit between the first hole dimension portion 105 and the first tube dimension portion 91 is transition fit or close fit. Here, while the class of the fit between the first hole dimension portion 105 and the first tube dimension portion 91 is the close fit, a maximum allowable value of the first hole dimension D4 of the first hole dimension defining portion 101 is smaller than a minimum allowable value of the first tube dimension R3 of the first tube dimension portion 91. Moreover, while the class of the fit between the first hole dimension portion 105 and the first tube dimension portion 91 is the transition fit, a minimum allowable value of the first hole dimension D4 is smaller than a maximum allowable value of the first tube dimension R3, and the minimum allowable value of the first tube dimension R3 is smaller than the maximum allowable value of the first hole dimension D4. Therefore, when the class of the fit between the first hole dimension portion 105 and the first tube dimension portion 91 is the transition fit or the close fit, the first tube dimension portion 91 does not move with respect to the first hole dimension defining portion 101. Therefore, the tube distal end Z1 (the first tube dimension portion 91) is firmly fixed to the hole defining portion 35 at the first node position B1. As described above, the tube distal end Z1 of the tube member 51 is connected to the hole defining portion 35 of the cylindrical member 22 without using any different (separate) members other than the cylindrical member 22 and the tube member 51.

Moreover, a class of fit between the second hole dimension portion 106 and the second tube dimension portion 92 is clearance fit. Here, while the class of the fit between the second hole dimension portion 106 and the second tube dimension portion 92 is the clearance fit, a maximum allowable value of the second tube dimension R4 of the second tube dimension portion 92 is smaller than a minimum allowable value of the second hole dimension D5 of the second hole dimension defining portion 102. Therefore, since the class of the fit between the second hole dimension portion 106 and the second tube dimension portion 92 is the clearance fit, a clearance having a sufficiently large size is acquired between the second hole dimension defining portion 102 and the second tube dimension portion 92. Therefore, even while the tube distal end Z1 of the tube member 51 is fixed to the hole defining portion 35, contact of the second tube dimension portion 92 with the second hole dimension defining portion 102 is effectively prevented. In consequence, a contact region between the outer peripheral portion 52 of the tube member 51 and the hole defining portion 35 decreases.

Therefore, the ultrasonic treatment device 1 of the above constitution produces the following effect, in addition to the effect similar to that of the first embodiment. That is, in the ultrasonic probe 3 of the ultrasonic treatment device 1, the class of the fit between the first hole dimension portion 105 and the first tube dimension portion 91 is the transition fit or the close fit. Therefore, the first tube dimension portion 91 does not move with respect to the first hole dimension defining portion 101. Therefore, the tube distal end Z1 (the first tube dimension portion 91) can firmly be fixed to the hole defining portion 35 at the first node position B1. Moreover, since the tube distal end Z1 is fixed as described above, the tube distal end Z1 of the tube member 51 is connected to the hole defining portion 35 of the cylindrical member 22 without using any different members other than the cylindrical member 22 and the tube member 51. Since any different members are not used to connect the tube distal end Z1 of the tube member 51 to the cylindrical member 22 (the ultrasonic probe 3), it is possible to realize simplification of the constitution of the ultrasonic probe 3 and decrease of manufacturing cost of the ultrasonic probe 3.

Moreover, the class of the fit between the second hole dimension portion 106 and the second tube dimension portion 92 is the clearance fit. Therefore, a clearance having a sufficiently large size can be acquired between the second hole dimension defining portion 102 and the second tube dimension portion 92. Therefore, even while the tube distal end Z1 of the tube member 51 is fixed to the hole defining portion 35, the contact of the second tube dimension portion 92 with the second hole dimension defining portion 102 is effectively prevented. In consequence, the contact region between the outer peripheral portion 52 of the tube member 51 and the hole defining portion 35 decreases. Therefore, when a vibration transmitting section 20 ultrasonically vibrates, friction between the hole defining portion 35 of the vibration transmitting section 20 (the cylindrical member 22) and the tube member 51 which is the non-vibrating member decreases. In consequence, heat generation between the hole defining portion 35 of the vibration transmitting section 20 and the tube member 51 can effectively be prevented.

(Modification of Second Embodiment)

Figure 28:
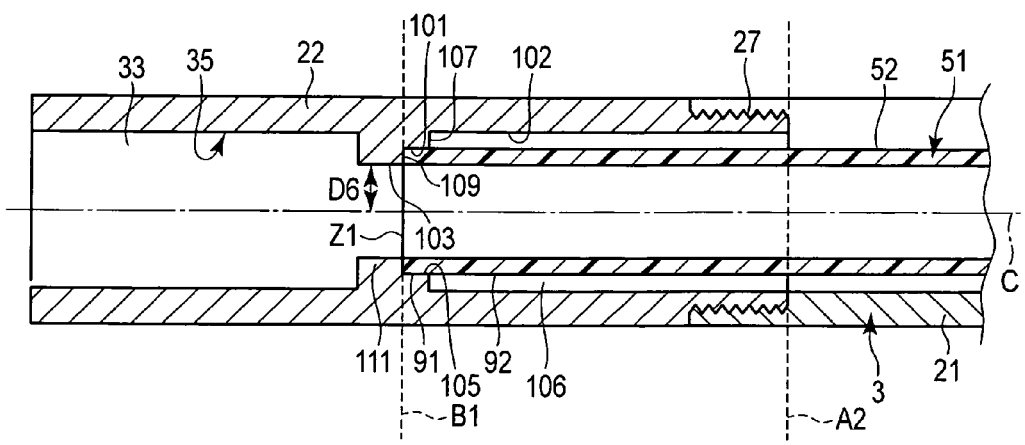
FIG. 28 is a cross-sectional view schematically showing an inner constitution of a cylindrical member of an ultrasonic probe according to a modification of the second embodiment.

It is to be noted that in the second embodiment, the third hole dimension defining portion 103 is extended up to the distal end of the cylindrical member 22 (the vibration transmitting section 20), but the present invention is not limited to this embodiment. For example, as a modification shown in FIG. 28, a projecting portion 111 projecting from a first hole dimension defining portion 101 toward an inner periphery direction may include a third hole dimension defining portion 103. In the present modification, a projecting end of the projecting portion 111 is the third hole dimension defining portion 103. In the third hole dimension defining portion 103, similarly to the second embodiment, a third hole dimension D6 between a longitudinal axis C and a hole defining portion 35 is smaller than a first hole dimension D4, and smaller than a first tube dimension R3 and a second tube dimension R4.

Moreover, the projecting portion 111 includes an intermediate surface 109 via which the first hole dimension defining portion 101 is continuous with the third hole dimension defining portion 103 at a first node position B1. By the intermediate surface 109, movement of a tube distal end Z1 toward a distal direction from the first node position B1 is regulated, and the tube distal end Z1 abuts on the intermediate surface 109. Consequently, in directions parallel to the longitudinal axis C, the tube distal end Z1 of a tube member 51 is disposed at about the same position as the first node position B1.

It is to be noted that the projecting portion 111 may be provided over the whole circumference around the longitudinal axis C. Moreover, two projecting portions 111 may be provided apart from each other around the longitudinal axis C. That is, the third hole dimension defining portion 103 extended toward the distal direction from the first node position B1 may be provided in at least a part around the longitudinal axis C.

As seen from the above modification of the second embodiment, the first hole dimension defining portion 101 including the first node position B1 may have the first hole dimension D4, and the second hole dimension defining portion 102 may have the second hole dimension D5 larger than the first hole dimension D4. Moreover, between the first hole dimension defining portion 101 and the second hole dimension defining portion 102, a hole dimension change portion (107), configured to change the dimension between the longitudinal axis C and the hole defining portion 35 from the first hole dimension D4 to the second hole dimension D5, may be provided. Furthermore, in the first hole dimension defining portion 101, a class of fit between the first hole dimension portion 105 and the first tube dimension portion 91 may be transition fit or close fit. Additionally, in the second hole dimension defining portion 102, a class of fit between the second hole dimension portion 106 and the second tube dimension portion 92 may be clearance fit.

According to the above constitution, as described above in the second embodiment, the tube distal end Z1 of the tube member 51 is connected to the hole defining portion 35 of the cylindrical member 22 without using any different (separate) members other than the cylindrical member 22 and the tube member 51. Moreover, even while the tube distal end Z1 of the tube member 51 is fixed to the hole defining portion 35, contact of the second tube dimension portion 92 with the second hole dimension defining portion 102 is effectively prevented. In consequence, a contact region between the outer peripheral portion 52 of the tube member 51 and the hole defining portion 35 decreases.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment device having a proximal end configured to be handled by a user and a distal end configured to contact a patient, the ultrasonic treatment device comprising:
    a vibration transmitting body having a longitudinal axis extending from a proximal direction toward a distal direction, wherein:
        a hole is formed inside the vibration transmitting body that extends from a distal portion of the vibration transmitting body to the proximal direction,
        the hole is surrounded by an inner surface of the vibration transmitting body and opens with respect to an outside of the vibration transmitting body at an opening, and
        the opening is located at the outside of the vibration transmitting body in the distal portion of the vibration transmitting body;
    a tube member having a first end and a second end, wherein:
        a passage is formed inside of the tube member and extends from the first end to the second end,
        the first end of the tube member is connected to the inner surface of the vibration transmitting body at a connected position in the hole of the vibration transmitting body,
        the tube member extends from the connected position toward the proximal direction inside of the vibration transmitting body,
        the tube member extends from inside of the vibration transmitting body to outside of the vibration transmitting body at an extended position that is located proximal to the connected position,
        the second end of the tube member is located outside of the vibration transmitting body, and
        the passage communicates with the opening of the hole; and
    a piezoelectric element attached to a proximal portion of the vibration transmitting body and located proximal to the connected position of the tube member and configured to generate an ultrasonic vibration and transmit the ultrasonic vibration to the vibration transmitting body,
    wherein the ultrasonic treatment device is configured such that:
        the vibration transmitting body is configured to transmit the ultrasonic vibration from the proximal portion to the distal portion,
        when the vibration transmitting body is configured to vibrate in a predetermined vibrating state, a first node position is located at the connected position of the tube member, and
        the predetermined vibrating state of the vibration transmitting body is configured to prevent transmission of the ultrasonic vibration to the tube member at the connected position.

2. The ultrasonic treatment device according to claim 1, wherein:
    the vibration transmitting body includes a horn that is located distal to the piezoelectric element, and in which a cross-sectional area perpendicular to the longitudinal axis decreases toward the distal direction, the horn being configured to enlarge an amplitude of the ultrasonic vibration when the ultrasonic vibration generated by the piezoelectric element is transmitted to the distal portion of the vibration transmitting body, and
    the connected position of the tube member is located distal to the horn.

3. The ultrasonic treatment device according to claim 2, wherein the extended position of the tube member is located between the connected position of the tube member and the horn along the longitudinal axis.

4. The ultrasonic treatment device according to claim 1, wherein:
    when the vibration transmitting body vibrates in the predetermined vibrating state, a plurality of node positions, include the first node position, are located in the vibrating transmitting body, and
    the first node position is located most distally among the plurality of node positions.

5. The ultrasonic treatment device according to claim 1, wherein:
    the extended position of the tube member is located between the connected position of the tube member and the piezoelectric element along the longitudinal axis,
    when the vibration transmitting body is configured to vibrate in the predetermined vibrating state, a plurality of node positions are located in the vibrating transmitting body,
    the plurality of node positions includes the first node position and a second node position that is different from the first node position, and
    when the vibration transmitting body is configured to vibrate in the predetermined vibrating state, the second node position is located at the extended position of the tube member.

* * * * *